US012597137B2

(12) United States Patent
Wang et al.

(10) Patent No.: US 12,597,137 B2
(45) Date of Patent: Apr. 7, 2026

(54) DIGITAL SYNTHESIS OF HISTOLOGICAL STAINS USING MULTIPLEXED IMMUNOFLUORESCENCE IMAGING

(71) Applicant: VENTANA MEDICAL SYSTEMS, INC., Tucson, AZ (US)

(72) Inventors: Xingwei Wang, Sunnyvale, CA (US); Zuo Zhao, Palo Alto, CA (US); Auranuch Lorsakul, Santa Clara, CA (US); Yao Nie, Sunnyvale, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 246 days.

(21) Appl. No.: 18/504,878

(22) Filed: Nov. 8, 2023

(65) Prior Publication Data

US 2024/0112341 A1 Apr. 4, 2024

Related U.S. Application Data

(63) Continuation of application No. PCT/US2022/032468, filed on Jun. 7, 2022.

(Continued)

(51) Int. Cl.
*G06K 9/00* (2022.01)
*G06T 7/00* (2017.01)
(Continued)

(52) U.S. Cl.
CPC .......... *G06T 7/0014* (2013.01); *G06T 11/001* (2013.01); *G16H 30/40* (2018.01);
(Continued)

(58) Field of Classification Search
CPC ................. G06T 7/0014; G06T 11/001; G06T 2207/10024; G06T 2207/10064;
(Continued)

(56) References Cited

U.S. PATENT DOCUMENTS 12,131,461 B2 * 10/2024 Izadyyazdanabadi ......................
A61B 1/063
2019/0392580 A1 * 12/2019 Kapil ................... G06V 20/695

FOREIGN PATENT DOCUMENTS

CN 110390631 A * 10/2019 ............... G06T 5/50
WO 2017212055 A1 12/2017
(Continued)

OTHER PUBLICATIONS

International Search Report and Written Opinion for PCT Application No. PCT/US2022/032468, dated Sep. 30, 2022.
(Continued)

*Primary Examiner* — Xin Jia
(74) *Attorney, Agent, or Firm* — Mughal Gaudry & Franklin PC

(57) ABSTRACT

Techniques for obtaining a synthetic histochemically stained image from a multiplexed immunofluorescence (MPX) image may include producing an N-channel input image that is based on information from each of M channels of an MPX image of a tissue section, where M and N are positive integers and N is less than or equal to M; and generating a synthetic image by processing the N-channel input image using a generator network, the generator network having been trained using a training data set that includes a plurality of pairs of images. The synthetic image depicts a tissue section stained with at least one histochemical stain. Each pair of images of the plurality of pairs of images includes an N-channel image, produced from an MPX image of a first section of a tissue, and an image of a second section of the tissue stained with the at least one histochemical stain.

20 Claims, 26 Drawing Sheets
(18 of 26 Drawing Sheet(s) Filed in Color)

Related U.S. Application Data

(60) Provisional application No. 63/212,039, filed on Jun. 17, 2021.

(51) Int. Cl.
  *G06T 11/00*    (2006.01)
  *G16H 30/40*    (2018.01)

(52) U.S. Cl.
  CPC ............... *G06T 2207/10024* (2013.01); *G06T 2207/10064* (2013.01); *G06T 2207/20081* (2013.01); *G06T 2207/20084* (2013.01); *G06T 2207/30024* (2013.01); *G06T 2207/30096* (2013.01)

(58) Field of Classification Search
  CPC . G06T 2207/20081; G06T 2207/20084; G06T 2207/30024; G06T 2207/30096; G16H 30/40
  See application file for complete search history.

(56) References Cited

FOREIGN PATENT DOCUMENTS

| | | | |
|---|---|---|---|
| WO | 2021061710 A1 | 4/2021 | |
| WO | WO-2021133847 A1 * | 7/2021 | .......... G06V 20/698 |

OTHER PUBLICATIONS

Isola, P. et al., "Image-to-Image Translation with Conditional Adversarial Networks", arXiv:1611.07004v1, Cornell University Library, Nov. 21, 2016.

Mercan, C. et al. "Virtual Staining for Mitosis Detection in Breast Histopathology", arXiv:2003.07801v1, Cornell University Libarary, Mar. 17, 2020.

Zhang, Y. et al. "Digital synthesis of histological stains using micro-structured and multiplexed virtual staining of label-free tissue", Light: Science & Applications, vol. 9, No. 78 (2020).

Office Action in Japanese Patent Application No. 2023-577709, dated Oct. 10, 2024.

Examination Report for European Patent Application No. 22740662.6 mailed Jan. 28, 2026.

* cited by examiner

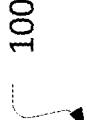
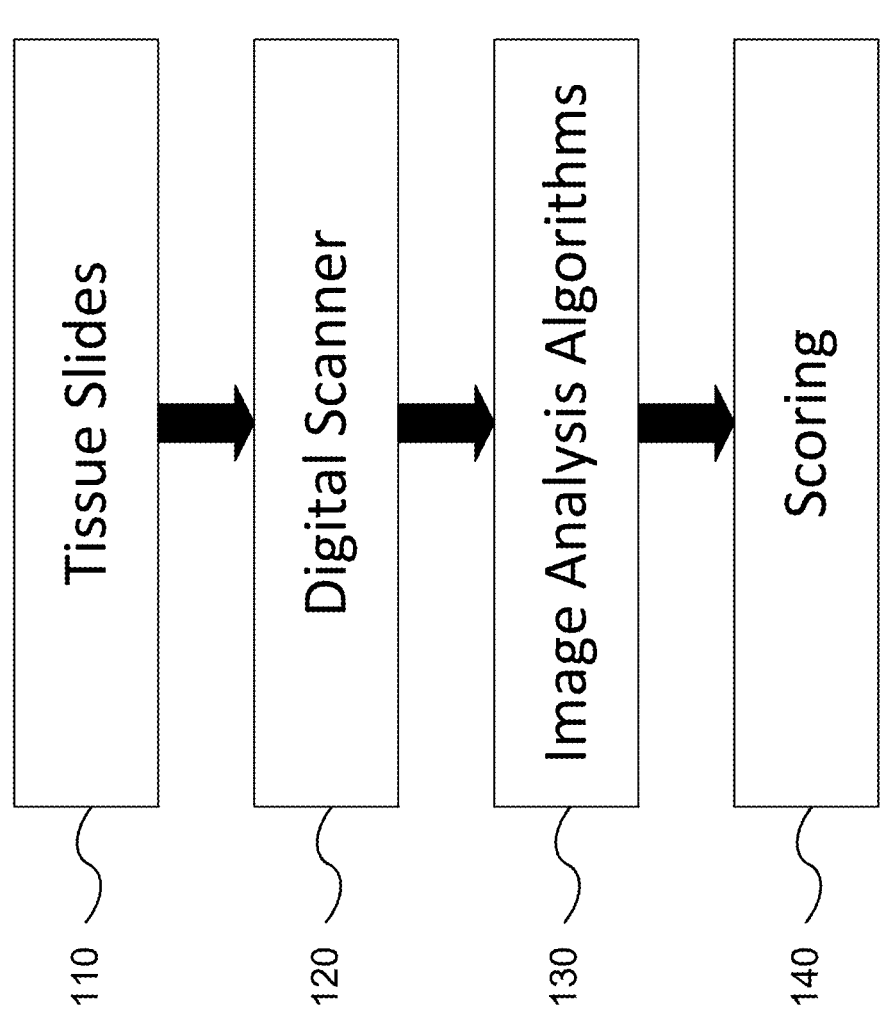
FIG. 1

DAPI　CD3　PD-L1　PD1　PanCK　Gzmb

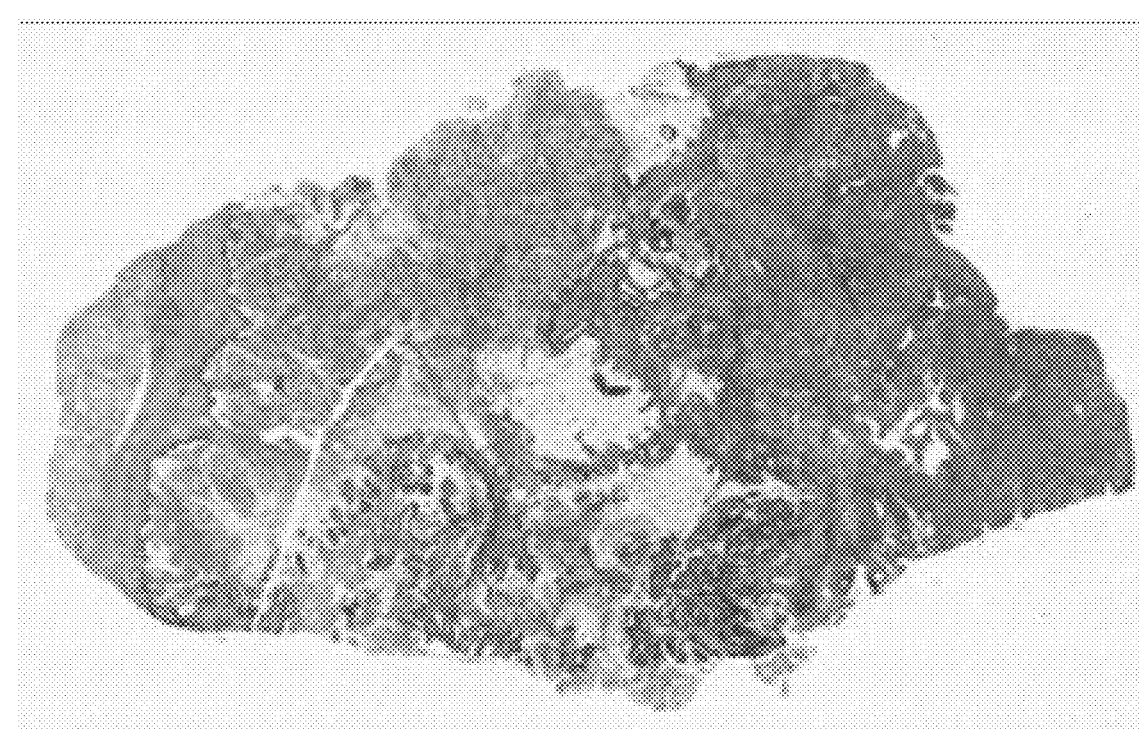
FIG. 5A
FIG. 5B
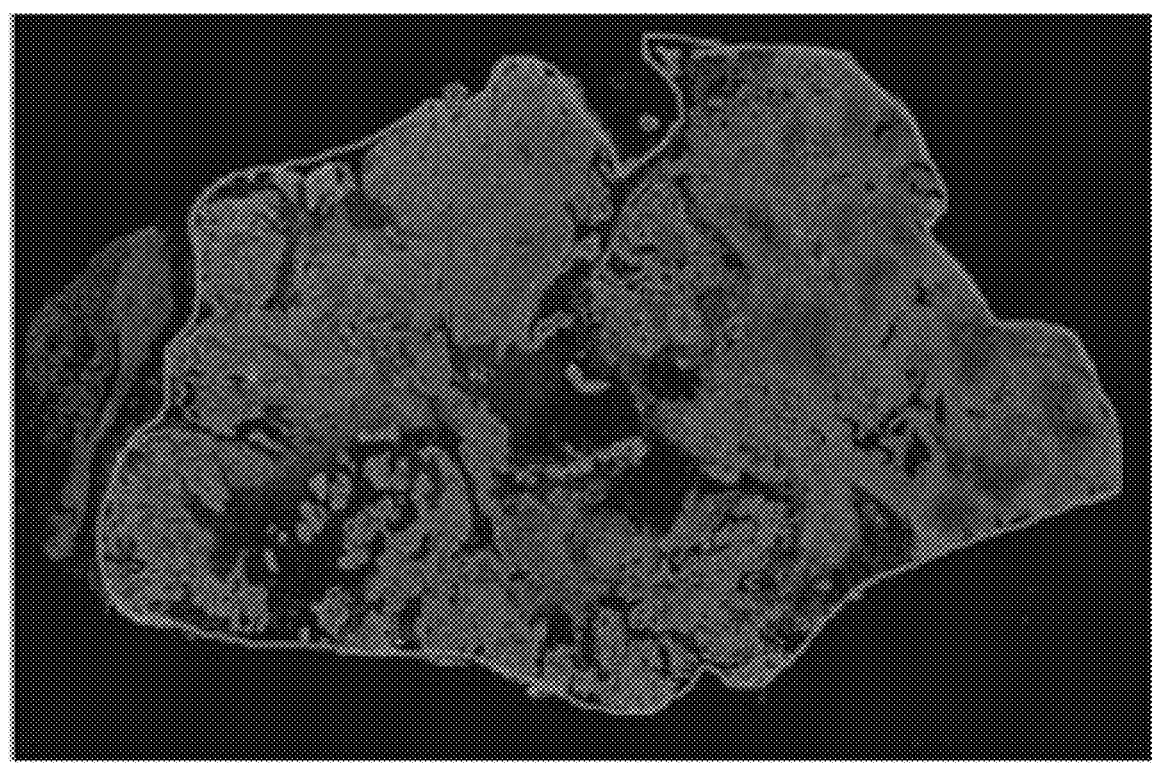

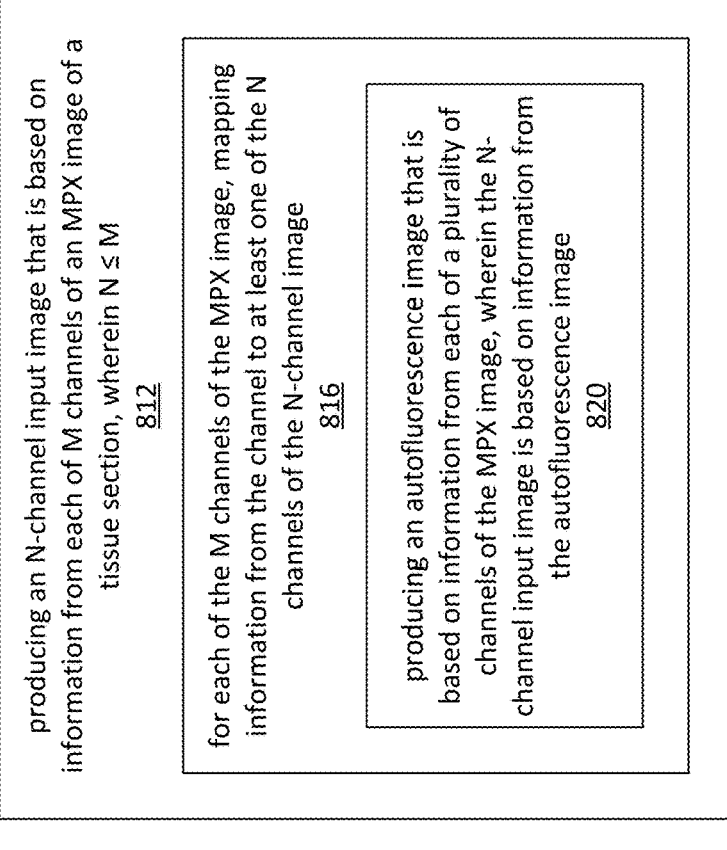

producing an N-channel input image that is based on information from each of M channels of an MPX image of a tissue section, wherein N ≤ M
812 for each of the M channels of the MPX image, mapping information from the channel to at least one of the N channels of the N-channel image
816 producing an autofluorescence image that is based on information from each of a plurality of channels of the MPX image, wherein the N-channel input image is based on information from the autofluorescence image
820

FIG. 8B producing an N-channel input image that is based on information from each of M channels of an MPX image of a tissue section, wherein N ≤ M
804 generating a synthetic image by processing the N-channel input image using a generator network, wherein the synthetic image depicts a tissue section that has been stained with at least one histochemical stain
808

AF image mapped to eosin color profile
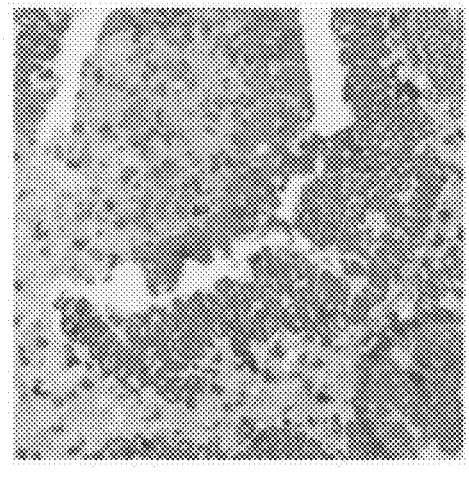
N-channel mapped image (pHE2)
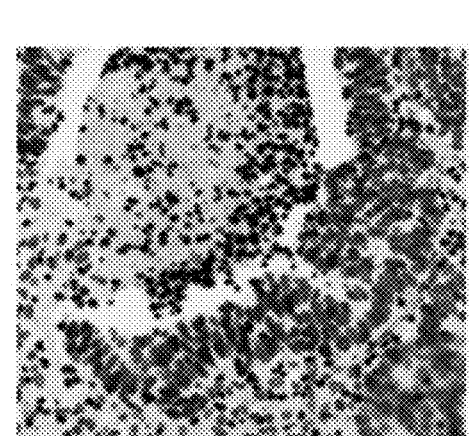
DAPI image mapped to hematoxylin color profile
FIG. 13

$T_{H\&E}$
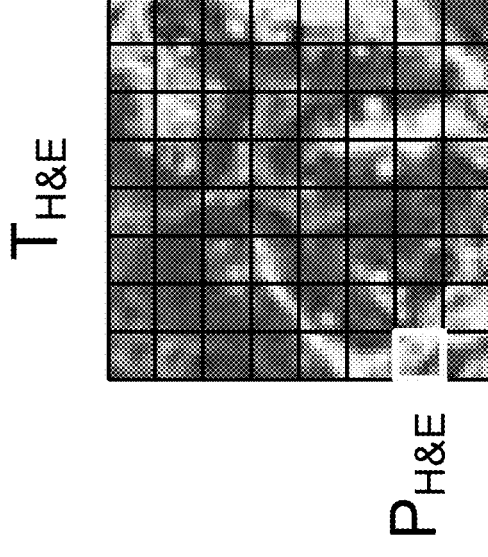
$P_{H\&E}$
$T_{Nmap}$
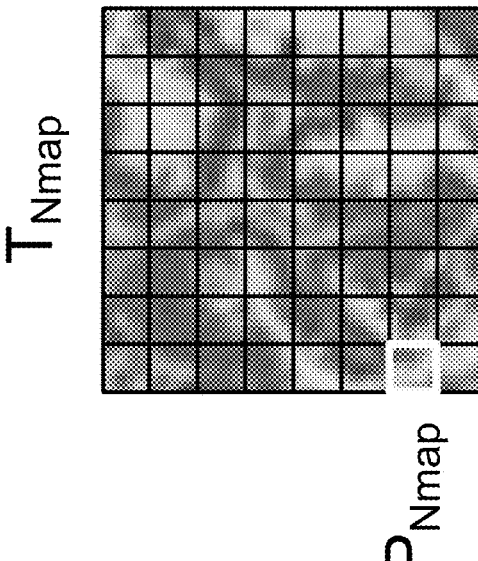
$P_{Nmap}$
FIG. 18

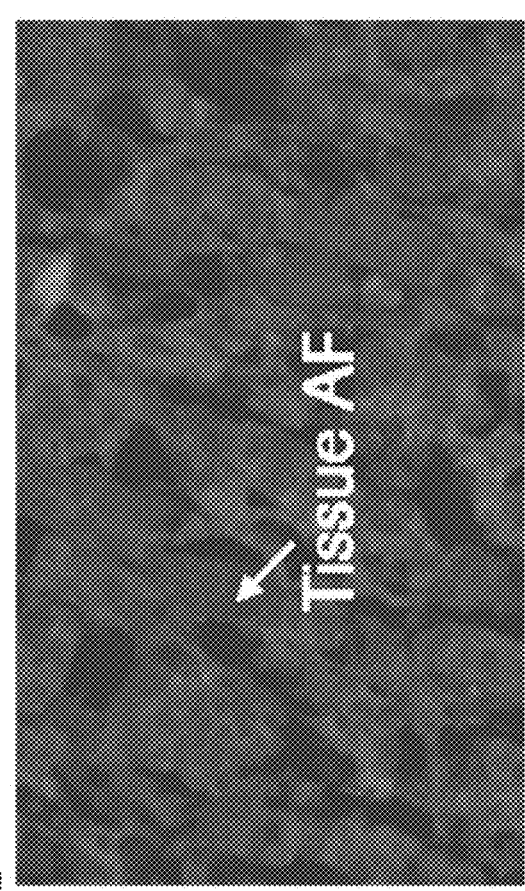
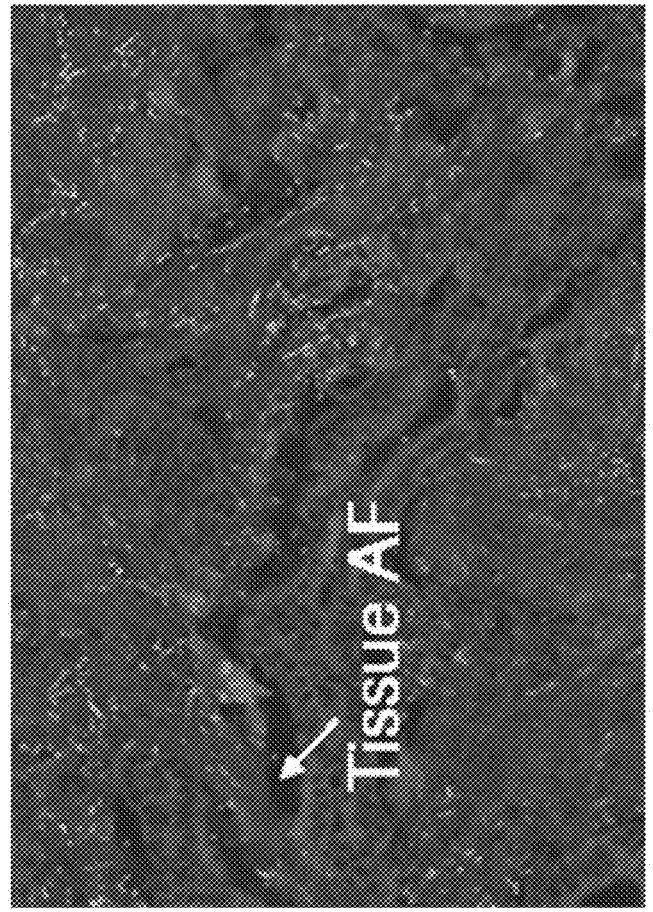
FIG. 25

Pancreas After AF Remove

Pancreas Before AF Remove

DIGITAL SYNTHESIS OF HISTOLOGICAL STAINS USING MULTIPLEXED IMMUNOFLUORESCENCE IMAGING

CLAIM FOR PRIORITY

This application is a continuation of and claims priority to PCT Patent Application No. PCT/US2022/032468, filed on Jun. 7, 2022, and titled "DIGITAL SYNTHESIS OF HISTOLOGICAL STAINS USING MULTIPLEXED IMMUNOFLUORESCENCE IMAGING", which claims priority to U.S. Provisional Application No. 63/212,039, filed on Jun. 17, 2021. Each of these applications are incorporated by reference in their entireties for all purposes.

FIELD

The present disclosure relates to digital pathology, and in particular to techniques that include obtaining a synthetic histologically stained image from a multiplexed immunofluorescence image.

BACKGROUND

Histopathology may include examination of slides prepared from sections of tissue for a variety of reasons, such as: diagnosis of disease, assessment of a response to therapy, and/or the development of pharmacological agents to fight disease. Because the tissue sections and the cells within them are virtually transparent, preparation of the slides typically includes staining the tissue sections in order to render relevant structures more visible. Digital pathology may include scanning of the stained slides to obtain digital images, which may be subsequently examined by digital pathology image analysis and/or interpreted by a human pathologist.

Multiplexed immunofluorescence (MPX) staining of tissue sections allows simultaneous detection of multiple biomarkers and their co-expression at a single-cell level. MPX enables characterizations of immune context in a tumor microenvironment, which may have significant influence on responses to immunotherapies. For example, the use of MPX can provide for detection of more biomarkers and co-localization in a single slide. While MPX promises to be a valuable tool for discovering effective treatments and developing new drugs, some challenges remain with respect to accurately associating MPX results with underlying tissue structures.

SUMMARY

In various embodiments, a computer-implemented method of image transformation is provided that includes producing an N-channel input image that is based on information from each of M channels of a multiplexed immunofluorescence (MPX) image of a tissue section, where M is a positive integer and N is a positive integer that is less than or equal to M; and generating a synthetic image by processing the N-channel input image using a generator network, the generator network having been trained using a training data set that includes a plurality of pairs of images. In this method, the synthetic image depicts a tissue section that has been stained with at least one histochemical stain, and for each pair of images of the plurality of pairs of images, the pair includes an N-channel image, produced from an MPX image of a first section of a tissue, and an image of a second section of the tissue that has been stained with the at least one histochemical stain.

In some embodiments, producing the N-channel input image comprises, for each of the M channels of the MPX image of the tissue section, mapping information from the channel to at least one of the N channels of the N-channel image. The mapping may include producing an autofluorescence image that is based on information from each of a plurality of channels (e.g., each of the M channels) of the MPX image of the tissue section, and the N-channel input image may be based on information from the autofluorescence image. The autofluorescence image may be based on a nonlinear combination of the plurality of channels of the MPX image of the tissue section. Additionally or alternatively, the autofluorescence image may be based on a spectral distribution of autofluorescence among the plurality of channels.

In some embodiments, the synthetic image is an N-channel image. Each of the N-channel input image and the synthetic image may be an RGB image. Additionally or alternatively, the MPX image of the tissue section may be a dark-field image and/or the synthetic image may be a bright-field image.

In some embodiments, the at least one histochemical stain is hematoxylin and eosin.

In some embodiments, the N-channel image is based on the autofluorescence image and on a nuclear counterstain image. For example, the N-channel image may be based on a linear combination of the autofluorescence image and on a channel of the MPX image of the tissue section that corresponds to a nuclear counterstain. The N-channel image is based on an array of optical density values that is based on the linear combination.

In some embodiments, N is equal to three and/or M is at least four.

In some embodiments, the generator network was trained as part of a generative adversarial network. In some embodiments, the generator network is implemented as a U-Net and/or as an encoder-decoder network. The generator network may be updated via L1 loss measured between an image by the generator network and an expected output image.

In some embodiments, a method is provided that includes determining, by a user, a diagnosis of a subject based on the synthetic image as generated by an embodiment of the computer-implemented method.

In some embodiments, a method is provided that includes determining, by a user, a diagnosis of a subject based on the synthetic image as generated by an embodiment of the computer-implemented method, and administering, by the user, a treatment with a compound based on (i) the synthetic image, and/or (ii) the diagnosis of the subject.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Aspects and features of the various embodiments will be more apparent by describing examples with reference to the accompanying drawings, in which:

FIG. 1 shows an example diagram of a digital pathology solution workflow;

FIGS. 5A and 5B show an MPX (dark-field) image (FIG. 5A) that is registered with an H&E (bright-field) image (FIG. 5B);

FIG. 8A illustrates a flowchart for an exemplary process according to some embodiments;

FIG. 8B illustrates a flowchart for another exemplary process according to some embodiments;

FIG. 13 illustrates a further process of producing a three-channel mapped input image according to some embodiments;

FIG. 18 shows an example of extraction of tiles and image patches from whole slide images according to some embodiments;

FIGS. 21-23 show examples of input images, target images, and output images generated according to various embodiments;

FIG. 25 shows two examples of MPX images of unstained tissue samples; and

DETAILED DESCRIPTION

Figure 2:
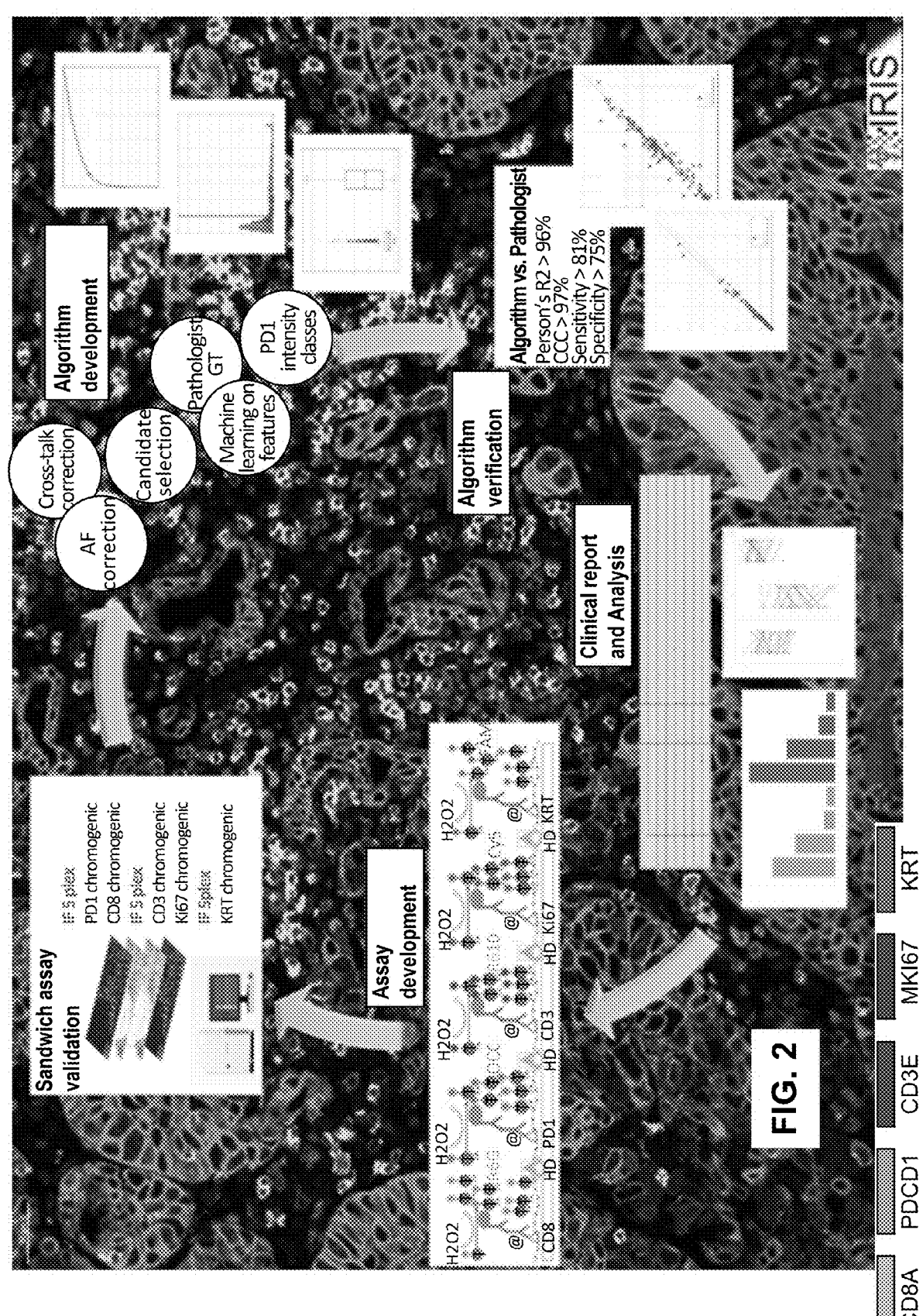
FIG. 2 shows an example diagram of a multiplexed immunofluorescence (MPX) imaging workflow and an example MPX image.

Systems, methods and software disclosed herein facilitate obtaining synthetic histologically stained images from multiplexed immunofluorescence images. While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

I. Overview

Digital pathology may involve the interpretation of digitized images in order to correctly diagnose subjects and guide therapeutic decision making. In digital pathology solutions, image-analysis workflows can be established to automatically detect or classify biological objects of interest (e.g., positive/negative tumor cells, etc.). FIG. 1 shows an example diagram of a digital pathology solution workflow 100. The digital pathology solution workflow 100 includes obtaining tissue slides at block 110, scanning preselected areas or the entirety of the tissue slides with a digital image scanner (e.g., a whole slide image (WSI) scanner) to obtain digital images at block 120, performing image analysis on the digital image using one or more image analysis algorithms at block 130, and scoring objects of interest based on the image analysis (e.g., quantitative or semi-quantitative scoring such as positive, negative, medium, weak, etc.) at block 140.

Evaluation of tissue changes caused, for example, by disease, may be performed by examining thin tissue sections. A tissue sample (e.g., a sample of a tumor) may be sliced to obtain a series of sections, with each section having a thickness of, for example, 4-5 microns. Because the tissue sections and the cells within them are virtually transparent, preparation of the slides typically includes staining the tissue sections in order to render relevant structures more visible. For example, different sections of the tissue may be stained with one or more different stains to express different characteristics of the tissue.

Each section may be mounted on a slide, which is then scanned to create a digital image that may be subsequently examined by digital pathology image analysis and/or interpreted by a human pathologist (e.g., using image viewer software). The pathologist may review and manually annotate the digital image of the slides (e.g., tumor area, necrosis, etc.) to enable the use of image analysis algorithms to extract meaningful quantitative measures (e.g., to detect and classify biological objects of interest). Conventionally, the pathologist may manually annotate each successive image of multiple tissue sections from a tissue sample to identify the same aspects on each successive tissue section.

One type of tissue staining is histochemical staining, which uses one or more chemical dyes (e.g., acidic dyes, basic dyes) to stain tissue structures. Histochemical staining may be used to indicate general aspects of tissue morphology and/or cell microanatomy (e.g., to distinguish cell nuclei from cytoplasm, to indicate lipid droplets, etc.). One example of a histochemical stain is hematoxylin and eosin (H&E). Other examples of histochemical stains include trichrome stains (e.g., Masson's Trichrome), Periodic Acid-Schiff (PAS), silver stains, and iron stains. Images of histochemically stained samples are typically obtained using bright-field microscopy, and slides of histochemically stained samples are typically scanned at a resolution of 8 bits per pixel per color channel (e.g., each of red, green, and blue (RGB)).

In an H&E-staining of a tissue sample, the hematoxylin stains the cell nuclei blue, while eosin stains the extracellular matrix and cytoplasm pink, and other structures may be stained to have different shades, hues, and/or combinations of pink and blue. While the H&E stain is useful for identifying general tissue and cell anatomy, however, it fails to provide the specific information needed to support certain diagnostic evaluations, such as information that can be used to distinguish between different types of cancer (e.g., HER2 scoring), which may be provided by immunohistochemistry as described below.

Another type of tissue staining is immunohistochemistry (IHC, also called "immunostaining"), which uses a primary antibody that binds specifically to the target antigen of interest (also called a biomarker). IHC may be direct or indirect. In direct IHC, the primary antibody is directly conjugated to a label (e.g., a chromophore or fluorophore). In indirect IHC, the primary antibody is first bound to the target antigen, and then a secondary antibody that is conjugated with a label (e.g., a chromophore or fluorophore) is bound to the primary antibody. The use of IHC for tissue staining typically requires the use of very expensive reagents and more complicated laboratory equipment and procedures than histochemical staining. Images of samples stained with IHC fluorophores are typically obtained using dark-field microscopy.

In multiplexed immunofluorescence (MPX) imaging, a single slide is stained with multiple IHC fluorophores, wherein the emission spectra of the various fluorophores are distinguishable from one another. The number of different fluorophores in an MPX panel is typically five or six, but may be less or more. In addition to the fluorophores that label the desired biomarkers, a fluorogenic nuclear counterstain is typically included, such as 4',6-diamidino-2-phenylindole (DAPI). The MPX image is obtained by capturing emissions from each fluorophore to a separate corresponding channel of the dark-field image (typically at a resolution of sixteen bits per pixel per channel), and the MPX image is viewed by assigning a different pseudocolor to each channel.

Figure 3:
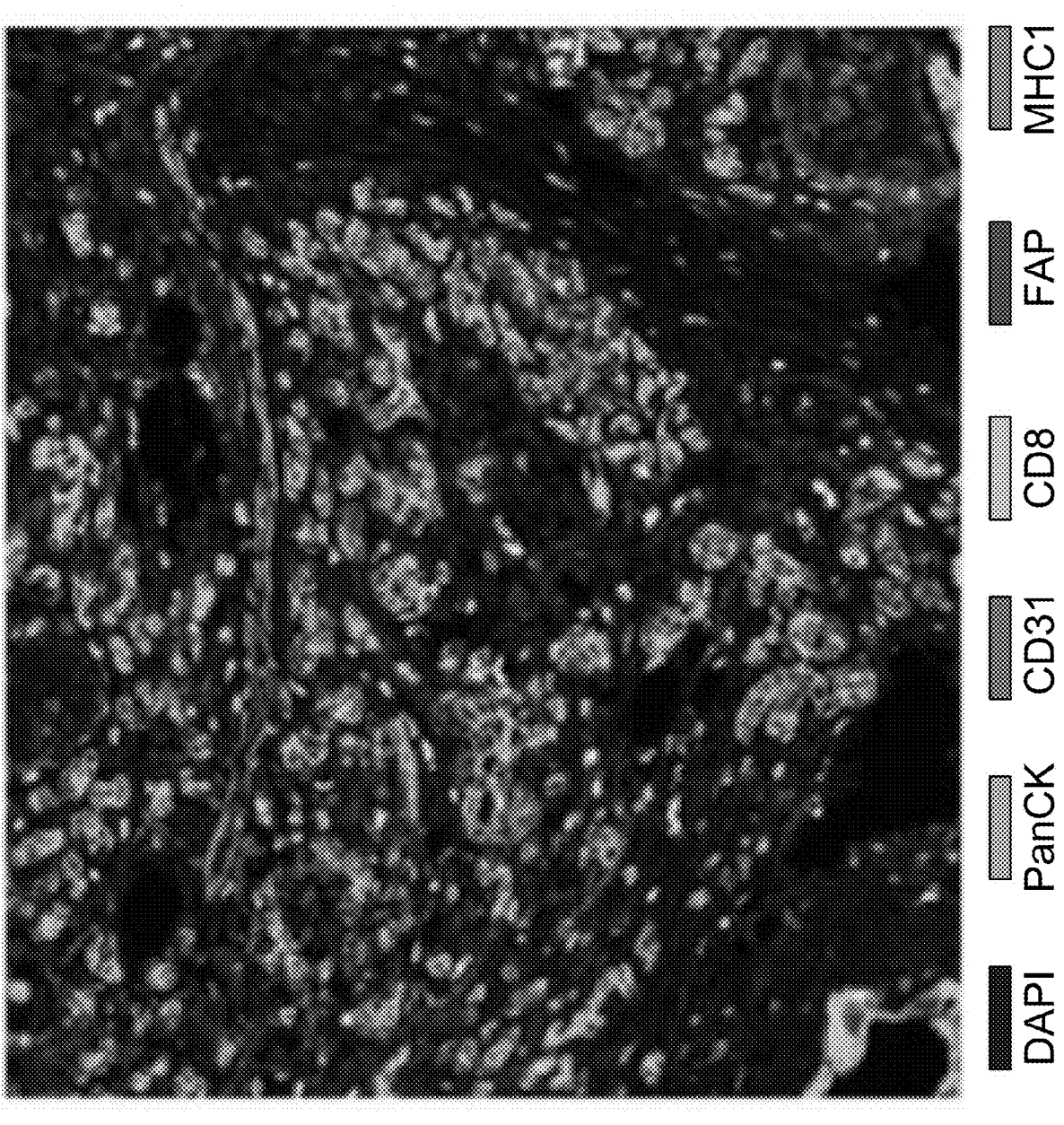
FIG. 3 shows an example MPX image of a slide from an MPX panel.
Figure 4:
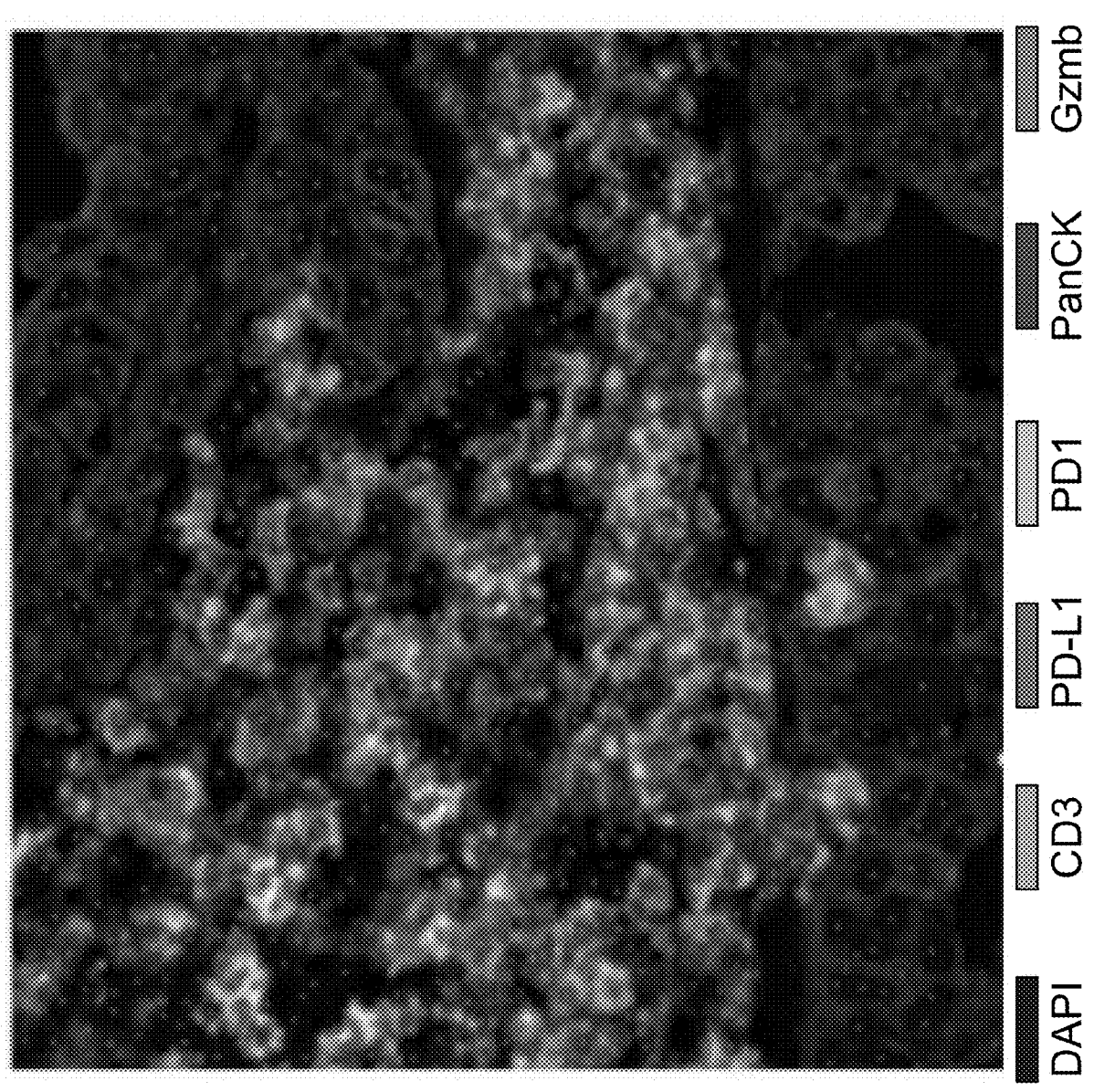
FIG. 4 shows another example MPX image of a slide from an MPX panel.

FIGS. 2, 3, and 4 show MPX images for three different panels of IHC stains. In the image of FIG. 2, the channels corresponding to biomarkers CD8A, programmed cell death protein 1 (PDCD1), cluster of differentiation 3-epsilon (CD3E), marker of proliferation Ki-67 (MKI67), and keratin (KRT) are assigned the pseudocolors yellow, light blue, violet, red, and green, respectively. In the image of FIG. 3, channels corresponding to the nuclear counterstain DAPI and the biomarkers PanCK, CD31, fibroblast activation protein alpha (FAP), and major histocompatibility complex 1 (MHC1) are assigned the pseudocolors dark blue, light blue, green, red, and pink, respectively. In the image of FIG. 4, channels corresponding to DAPI and the biomarkers CD3 (light blue), programmed death-ligand 1 (PD-L1), PD1, PanCK, and granzyme B (Gzmb) are assigned the pseudocolors dark blue, light blue, green, yellow, red, and pink, respectively.

As compared to IHC, the detection of multiple biomarkers (e.g., as shown in FIGS. 2-4) in a single MPX slide provides valuable information regarding co-location and co-expression of biomarkers. For example, detection of five biomarkers at the same time allows for detection of a large number (e.g., 17 to 90) of phenotypes (co-expression of a defined set of biomarkers) in a single MPX slide.

FIG. 2 also shows an example of an MPX imaging workflow. Such a workflow may begin with algorithm development (e.g., including crosstalk correction, autofluorescence correction, candidate selection, pathologist ground-truth, machine learning on features, and/or PD1 intensity classes) and proceed through algorithm verification (e.g., comparing results from the algorithm with pathologist results), clinical reporting and analysis, and assay development followed by sandwich assay validation.

Figure 6:
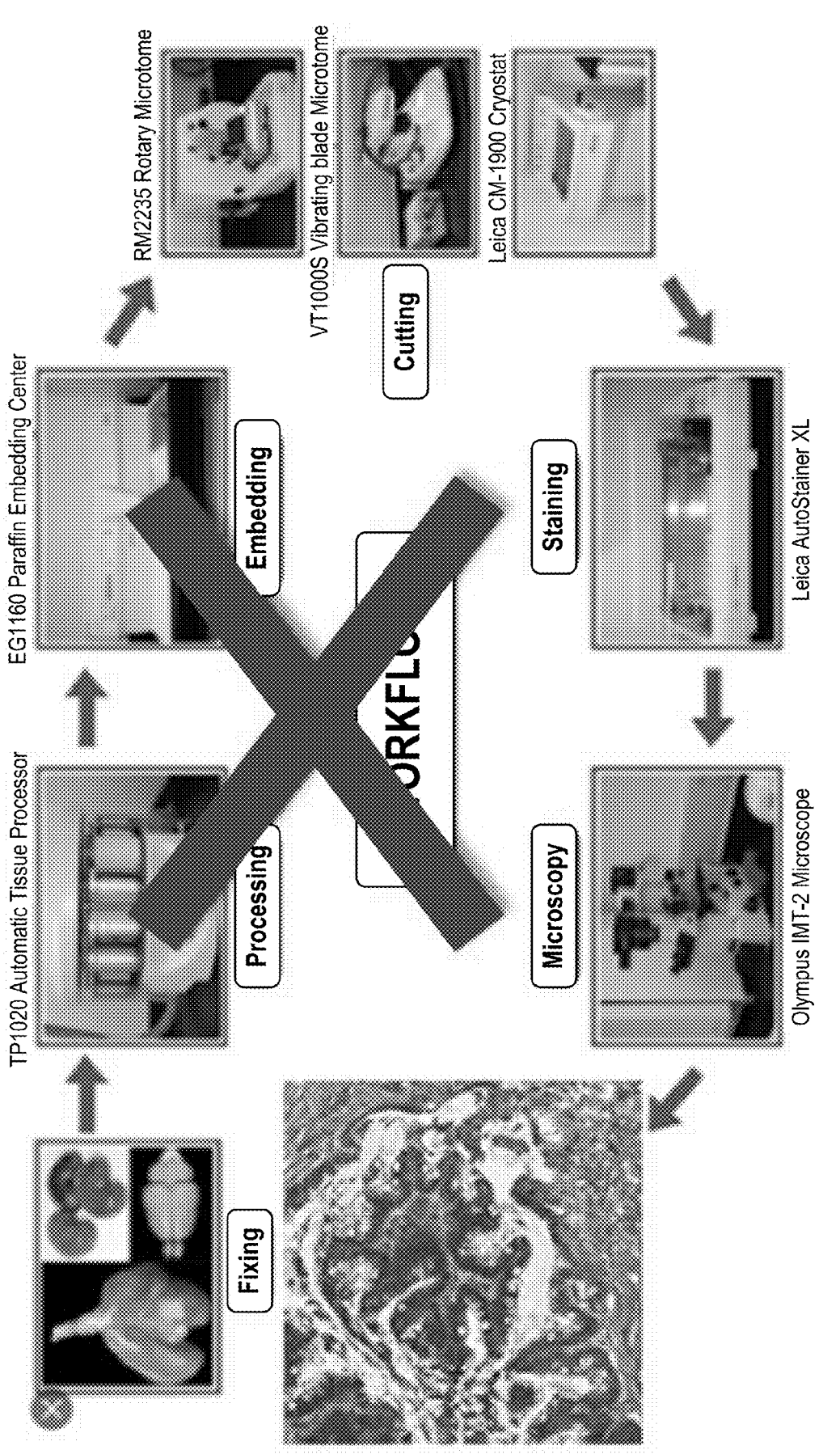
FIG. 6 shows an example of a workflow for obtaining an image of an H&E-stained sample.

Unlike histochemically stained (e.g., H&E) images, MPX images typically lack a clear depiction of underlying tissue structure. Consequently, the task of annotating an MPX image to delineate regions of interest (ROIs) for further analysis (e.g., tumor or epitumor regions) and/or regions to be excluded from further analysis (e.g., necrotic regions) can be difficult or impossible in isolation. For such reasons, the current practice of annotating an MPX image, or confirming a diagnosis based on an MPX image, commonly relies on a corresponding image of a nearby section of the sample that has been H&E-stained to provide the necessary structural details. The H&E image is registered to the MPX image so that the pathologist can easily toggle between the two images on a display (e.g., while performing the annotation). FIG. 6 shows an example of a workflow for producing an H&E image, which may include operations such as fixing, processing, embedding, cutting, staining, and microscopy.

FIG. 5A shows an example of an annotated MPX image, and FIG. 5B shows an example of a corresponding image of a nearby section of the sample that has been H&E-stained and registered to the MPX image. Preparation of the reference H&E image incurs extra cost, and review of the two images may require a pathologist to review additional tissue annotations. Registering one image to the other may be time-consuming and computationally expensive, as unique global and/or local deformations of each section may arise during the procedure of slide preparation. If the registration is inaccurate, then the spatial relationships between the biomarkers and the underlying tissue structure (e.g., cell membranes, nuclei) that are indicated when the registered images are overlaid, toggled, or otherwise viewed together may also be inaccurate. Moreover, even if the images are optimally registered, the two images will not depict the same tissue space because they are from different sections. Structures in one section may not be present in the other (e.g., structures whose size is comparable to the thickness of each section) or may have a different size and/or morphology in the other section, so that an overlay of the registered image with the baseline image may not truly capture the locations of the biomarkers relative to tissue structure, which may lead to difficulties during annotation and/or review of the MPX image.

Figure 7B:
FIGS. 7A and 7B show examples of a mapped image that resembles an H&E image and an actual H&E image, respectively.
Figure 7A:
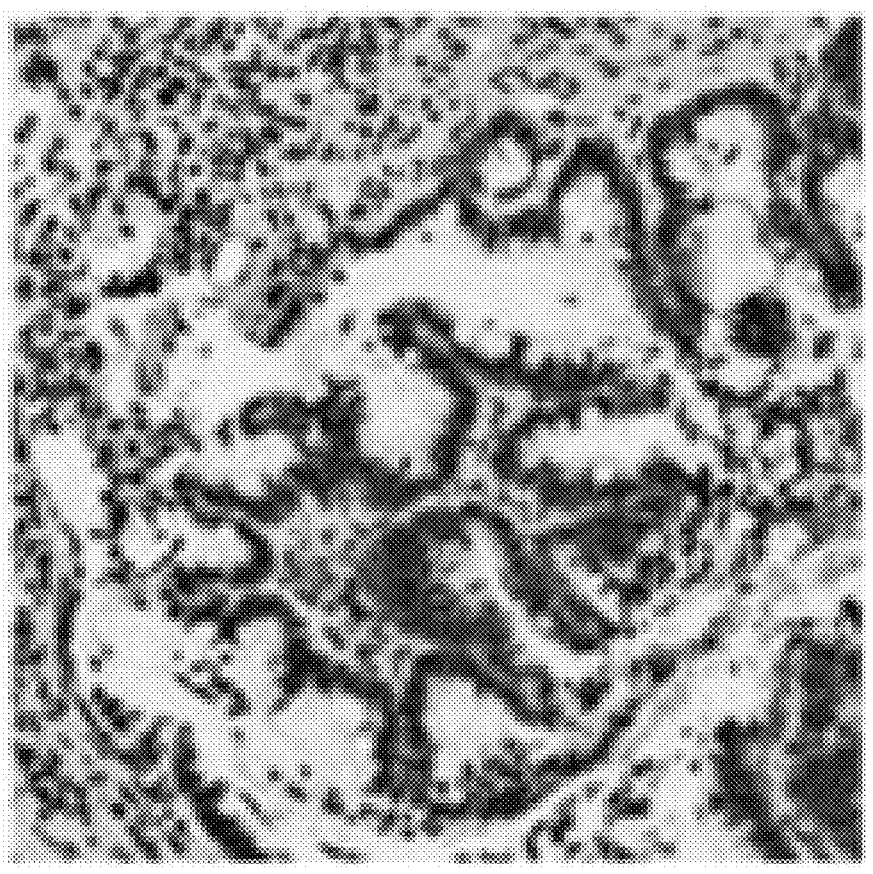

Conventional image processing techniques can be used to create an image that resembles an H&E-stained sample by mapping one or more channels of an MPX image to RGB color space. FIG. 7A shows an example of such a mapped image, and FIG. 7B shows a true H&E stained image for comparison. While a mapped image as shown in FIG. 7A may superficially resemble an H&E image, however, pathologists in routine clinical practices have confirmed that such an image shows insufficient image reality and quality to support, for example, an actual decision in diagnosis. By comparing the regions close to the right edges of the images in FIGS. 7A and 7B, for example, it may be seen that the mapped image of FIG. 7A lacks much of the structural detail which is evident in the mid-level values of FIG. 7B.

In order to overcome these limitations as well as others, techniques are disclosed herein for generating, from an MPX image, a synthetic (virtually stained) image that depicts a histochemically stained (e.g., H&E-stained) sample with a high degree of structural similarity to an actual image of a histochemically stained sample. Generation of such a synthetic image may support avoiding a complex and tedious tissue preparation and staining process as well as a registration operation. Clinically, such a solution may have an advantage of allowing the H&E staining tissue structure to be visualized by toggling the MPX image on and off, which meets pathologists' standard practice, and may promote clinical adoption of multiplex imaging. Developmentally, such a solution has a potential to generate ground truth for H&E analysis for algorithm developments and may enable easier registration of an MPX image to another MPX image, which can support discovering biomarkers.

Generation of the synthetic image may be performed by a trained generator network, which may include parameters learned while training a Generative Adversarial Network (GAN). The GAN may further include a discriminator network configured to predict whether an input image is fake (i.e., has been generated by the generator network) or real (i.e., depicts an actual image collected from a subject). Feedback based on the accuracy of these predictions can be provided to the generator network during training.

One illustrative embodiment of the present disclosure is directed to a method of image transformation that includes producing an N-channel input image that is based on information from each of M channels of an MPX image of a tissue section, where M is a positive integer and N is a positive integer that is less than or equal to M; and generating a synthetic image by processing the N-channel input image using a generator network, the generator network having been trained using a training data set that includes a plurality of pairs of images. In this method, the synthetic image depicts a tissue section that has been stained with at least one histochemical stain, and for each pair of images of the plurality of pairs of images, the pair includes an N-channel image, produced from an MPX image of a first section of a tissue, and an image of a second section of the tissue that has been stained with the at least one histochemical stain.

II. Definitions

As used herein, when an action is "based on" something, this means the action is based at least in part on at least a part of the something.

As used herein, the terms "substantially," "approximately," and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, the term "sample," "biological sample," or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

III. Techniques for Digital Synthesis of Histological Stains Using MPX Imaging An approach to digital synthesis of histological stains using MPX imaging as described herein may use techniques of multi-modality transfer to translate from dark-field imaging of MPX to bright-field imaging of H&E staining. Such an approach uses information from different image channels to obtain intermediate and preprocessed training data for input to a deep learning network (e.g., a generative adversarial network or GAN). Such an approach may include using information from many or all of the channels of the MPX image to generate the input training datasets.

FIG. 8A illustrates a flowchart for an exemplary process 800 to transform a source image (e.g., a source image from a set of source images to be processed) into a new image (e.g., a new image of a set of new images to be generated) having characteristics similar to a target image. Process 800 may be performed using one or more computing systems, models, and networks (e.g., as described herein with respect to FIGS. 14-16, 19, and 20).

With reference to FIG. 8A, at block 804, an N-channel input image is produced that is based on information from each of M channels of an MPX image of a tissue section, where M is a positive integer and N is a positive integer that is less than or equal to M. At block 808, a synthetic image is generated by processing the N-channel input image using a generator network. The synthetic image depicts a tissue section that has been stained with at least one histochemical stain. The generator network has been trained using a training data set that includes a plurality of pairs of images, in which each pair includes an N-channel image, produced from an MPX image of a first section of a tissue (e.g., based on information from each of M channels of the MPX image of the first section), and an image of a second section of the tissue that has been stained with the at least one histochemical stain.

It may be desired for the number of channels N in the input image produced at block 804 to be equal to the number of channels in the synthetic image generated at block 808. For example, it may be desired to implement block 808 using a generator network, such as a Pix2Pix GAN, that is configured to produce an output image having the same number of channels as the input image. The synthetic image may be a three-channel image, such as an RGB image having a red channel (R), a green channel (G), and a blue channel (B).

FIG. 8B illustrates an implementation 812 of process block 804 that comprises a block 816. At block 816, for each of the M channels of the MPX image of the tissue section, information from the channel is mapped to at least one of the N channels of the N-channel image. Such mapping may include linear and/or nonlinear mapping. In this example, block 816 comprises a block 820. At block 820, an auto-fluorescence image is produced that is based on information from each of a plurality of channels (e.g., from each of the M channels) of the MPX image of the tissue section. In this implementation of process block 804, the N-channel input image is based on information from the autofluorescence image. An instance of block 812 may also be executed to produce each of the input images of the training data set from a corresponding one of a source set of MPX images.

In some embodiments of process 800, the histochemical stain is hematoxylin and eosin.

In some embodiments of process 800, the generator network was trained as part of a generative adversarial network (e.g., a cGAN, a Pix2Pix GAN, or a CycleGAN).

The autofluorescence image may be produced (e.g., at block 820) as a nonlinear combination of the plurality of channels of the MPX image. In one example, the plurality of channels of the MPX image are nonlinearly combined by selecting, for each pixel of the autofluorescence image, the minimum among the values of the corresponding pixels of the plurality of channels of the MPX image. This operation may be expressed, for example, as $b(x,y)=\min[a_1(x,y), a_2(x, y), \ldots, a_M(x,y)]$ for all pixel locations (x,y) (where a denotes the MPX image and b denotes the autofluorescence image). This operation is not linear. Producing the autofluorescence image may also include performing one or more operations on the image that results from the nonlinear combination (e.g., a noise reduction operation, such as applying a median filter).

Figure 9:
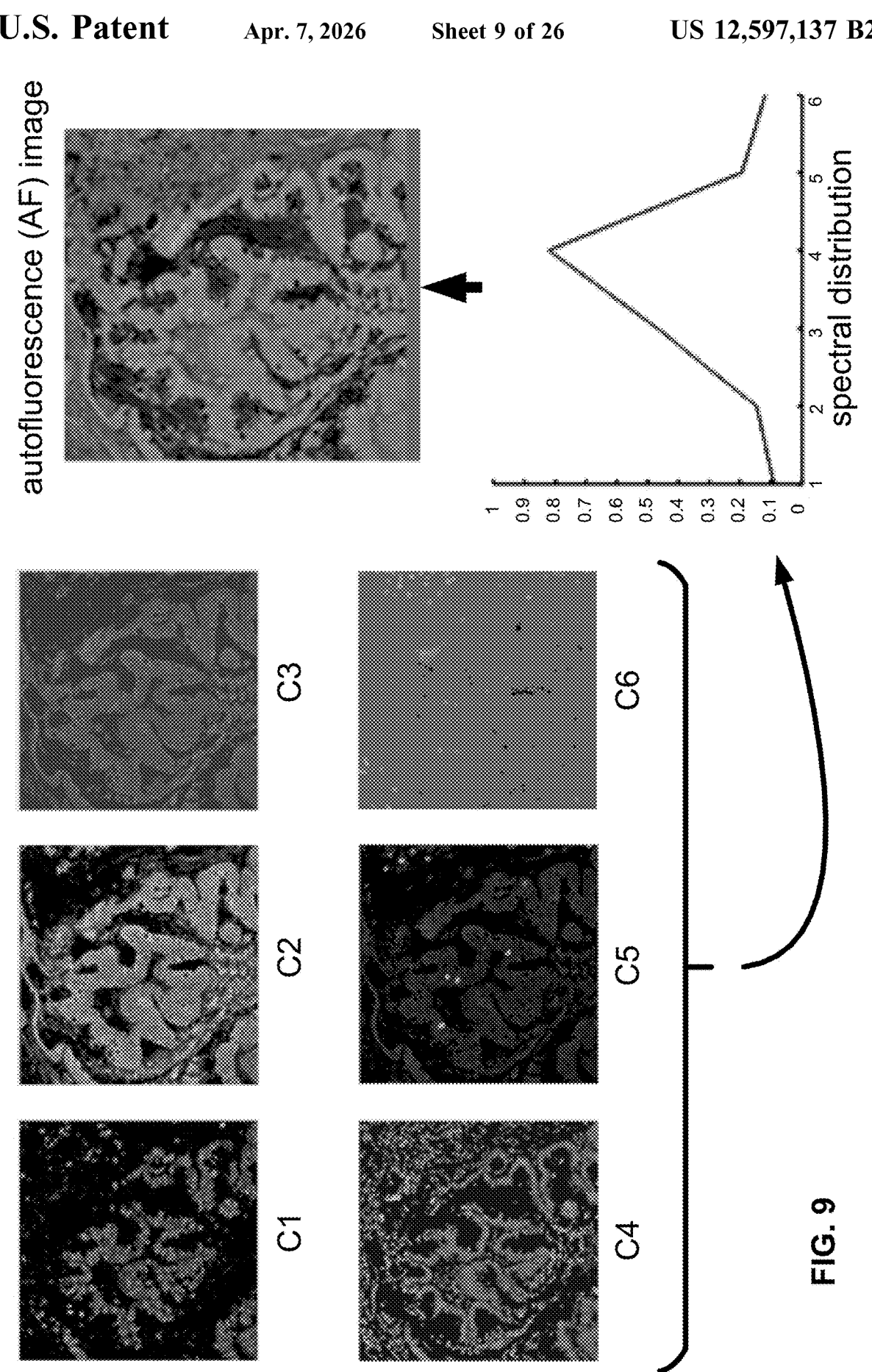
FIG. 9 illustrates a process of producing an autofluorescence image according to some embodiments.

FIG. 9 illustrates an example of a process of producing an autofluorescence image according to some embodiments. It may be desired for such a process to include equalizing the channels of the MPX image (e.g., to compensate for a variation among the levels of tissue autofluorescence as recorded at the various channels). In the example as shown in FIG. 9, the M channels of the MPX image are equalized before being nonlinearly combined (by, e.g., selecting the minimum pixel values as described above) to produce the autofluorescence image. As shown in FIG. 9, the equalization that is applied to the various channels of the MPX image may be determined according to a reference spectral distribution for the autofluorescence. For example, the equalization may be performed by dividing each channel of the MPX image by a corresponding weight (e.g., scaling factor), where the values of the weights for each of the various channels may be determined according to a given autofluorescence reference spectral distribution for the autofluorescence. The reference spectral distribution may be selected according to the tissue type of the sample in the MPX image, and calculation of the weights for the various channels as elements of an autofluorescence reference vector is described in more detail below.

In the particular example shown in FIG. 9, M is equal to six, and each of the six channels corresponds to a different one of six fluorophores (five biomarkers with their corresponding fluorophores and one fluorogenic nuclear counterstain (DAPI)). The staining protocol that is used to produce such an MPX image may also be referred to as a five-plex assay or panel. In other examples, M may be equal to three, four, or five (e.g., corresponding to a two-plex, a three-plex, and a four-plex assay or panel, respectively) or may be greater than six (e.g., seven, eight, nine, or ten or more). In the particular example shown in FIG. 9, the channel labeled 4 (four) is the DAPI channel.

Figure 24:
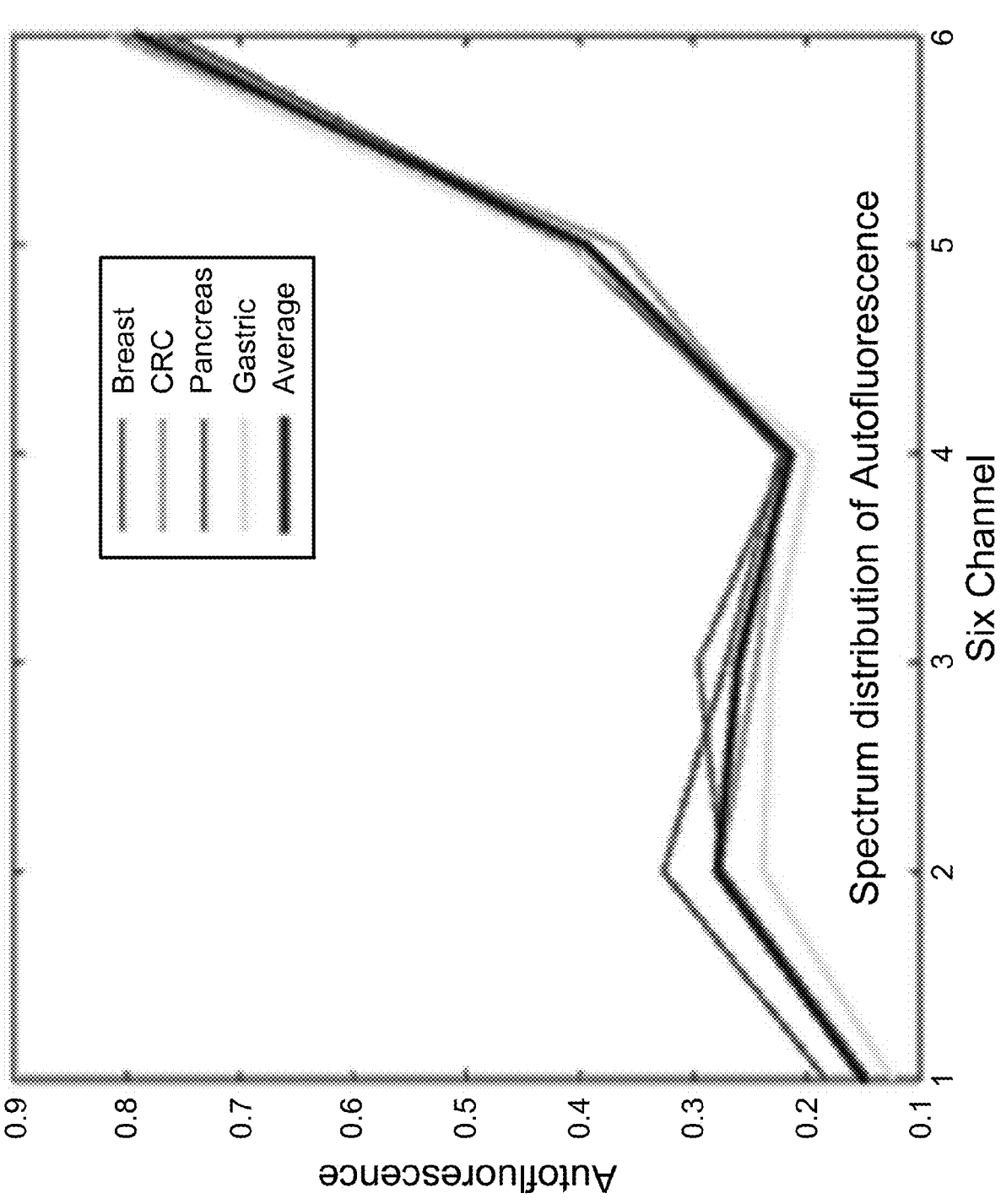
FIG. 24 shows comparative examples of reference spectral distributions of autofluorescence for four different kinds of tissue.

FIG. 24 shows comparative examples of reference spectral distributions of autofluorescence for four different kinds of tissue (breast, colorectal cancer (CRC), pancreas, and gastric), and the average of these distributions, for another six-channel system (in this figure, the channel labeled 6 (six) is the DAPI channel). The reference spectral distribution may be obtained from a reference MPX image of an unstained sample that is the same type of tissue (e.g., from the same tumor) as the stained sample depicted in the MPX image. FIG. 25 shows two examples of MPX images of unstained tissue samples. The reference MPX image may be captured using, for example, the same imaging system that is used to capture the MPX image of the stained sample.

The reference spectral distribution may be obtained as an autofluorescence reference vector (e.g., an M-element reference vector), wherein each element of the vector corresponds to a different channel of the reference MPX image and represents a relative degree of the tissue autofluorescence in that channel. The relative degree may be, for example, linear, polynomial, or exponential (e.g., magnitude, energy, or power). For the example shown in FIG. 9, the six elements of the autofluorescence reference vector (which may be applied as weights to the corresponding channels of the MPX image as described above) have the values [0.0919185036025541 0.147589073045573 0.467635814185659 0.822229790703801 0.195309012162166 0.120506922298875]. The particular area of the reference MPX image over which the relative degrees of autofluorescence are determined may be the entire image or a selected region of interest of the image (e.g., a tumor region or other annotated region). Each of the relative degrees of autofluorescence may be calculated as the value of a selected statistic (e.g., an average, such as arithmetic mean, median, etc.) of the values of the corresponding channel over the desired image area.

It may be desired to normalize each channel of the reference MPX image over the desired image area prior to calculating the statistic. In one such example, each channel is normalized separately to the range of from zero to one by min-max scaling (i.e., by identifying the maximum and minimum pixel values of the channel over the desired image area, and normalizing each value of the channel within the area by subtracting the minimum pixel value and dividing the result by the difference between the minimum and maximum pixel values).

While it is possible that the number of channels in the source MPX image is greater than M, it may be desired to use information from each one of all of the channels of the MPX image to produce the N-channel input image, and likewise for each of the N-channel training images. In other words, it may be desired for M to be equal to the total number of channels in the source MPX images. Such maximal use of information from all channels of the source MPX images to produce the training data may be important for obtaining a generator network that is trained to generate synthetic images having a maximum degree of structural similarity to the corresponding target images. Similarly, while it is possible for the number of channels that are combined to produce the autofluorescence image to be less than M, it may be desired to combine all of the M channels to produce the autofluorescence image.

Figure 10B:
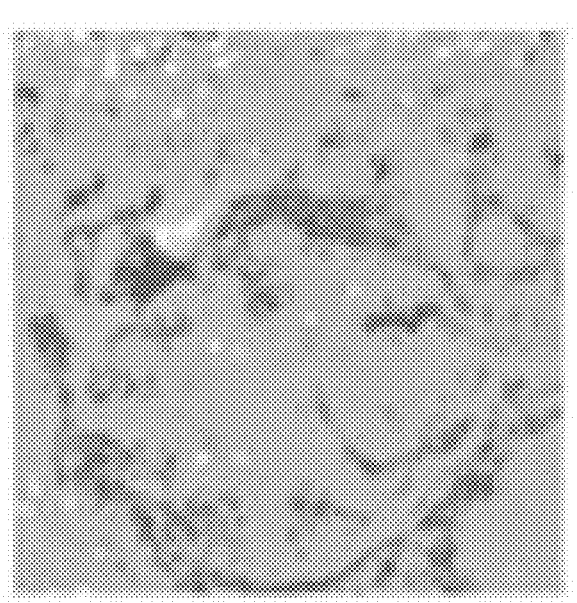
FIGS. 10A-10D show examples of three-channel (RGB) mapped input images, each obtained from a different corresponding mapping of M channels of an MPX image according to some embodiments.
Figure 10D:
Figure 10A:
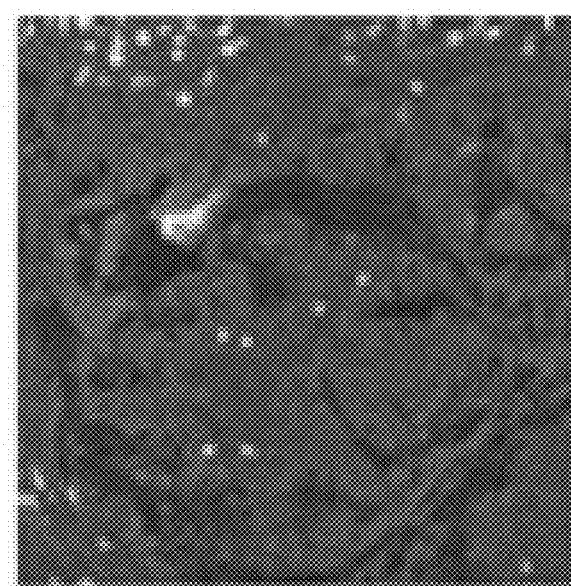
Figure 10C:

Examples of the mapped input images are now described. FIGS. 10A-10D show four examples of three-channel (RGB) images, each obtained based on information from six channels of an MPX image of an IHC-stained tissue section according to a different corresponding mapping according to some embodiments. Each of these four examples is based on a different linear combination of the autofluorescence image and the image from the DAPI (or other nuclear counterstain) channel of the MPX image. In the discussion herein, the mapping as shown in FIG. 10A is identified as "AF+AF+DAPI" or AAD, the mapping as shown in FIG. 10B is identified as "AF+DAPI+DAPI" or ADD, the mapping as shown in FIG. 10C is identified as "pseudo H&E" or pHE, and the mapping as shown in FIG. 10D is identified as "pseudo H&E 2" or pHE2.

Before performing a linear combination of the autofluorescence image and the DAPI image as described herein (e.g., with reference to FIGS. 11-13), it may be desired to rescale the autofluorescence image and the DAPI image to a specified range (alternatively, to rescale the autofluorescence image and the MPX image to a specified range). In one example, the rescaling may be a normalization, which may be performed by identifying the minimum and maximum pixel values of the image, and normalizing the pixel values of the image to the range of from zero to one (e.g., by min-max scaling as described herein). In another example, rescaling may be performed by applying a desired scaling factor to each pixel value of the image (e.g., to rescale the pixel values of the image from the range of from zero to 65535 to the range of from zero to 2000, or from zero to 3000, etc.).

Figure 26:
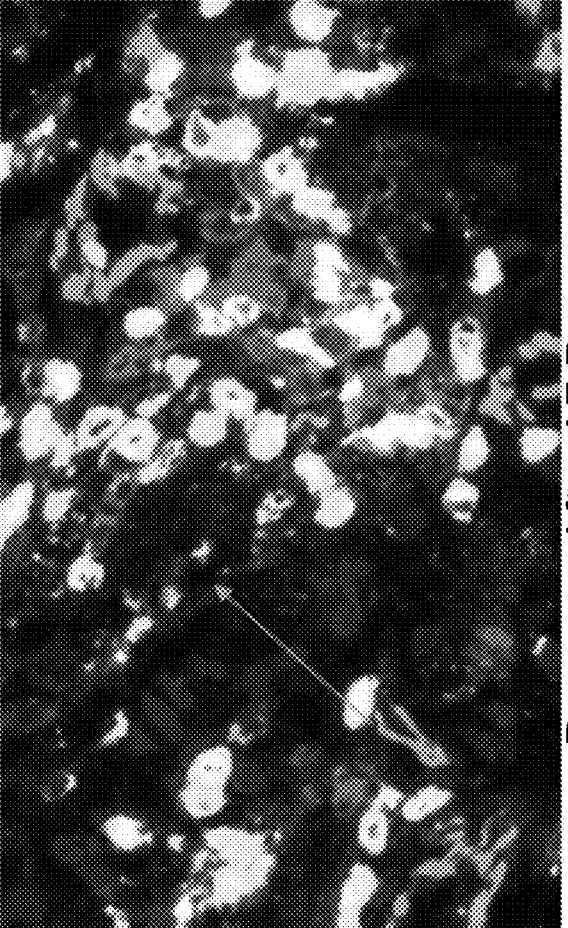
FIG. 26 shows an example of an MPX image of a pancreatic tissue sample before and after correction.

Before performing a linear combination of the autofluorescence image and the DAPI image as described herein (e.g., with reference to FIGS. 11-13), it may be desired to correct the DAPI image or to correct the MPX image (e.g., to compensate for the tissue autofluorescence). Such correction may be performed before or after a rescaling of the DAPI or MPX image as described above. Correction of the DAPI image may be performed by multiplying the autofluorescence image by the corresponding element of the autofluorescence reference vector to obtain a weighted autofluorescence image and subtracting, from each pixel value of the DAPI image, the corresponding pixel value of the weighted autofluorescence image to obtain the corrected DAPI image. Correction of each channel of the MPX image may be performed similarly by multiplying the autofluorescence image by the corresponding element of the autofluorescence reference vector to obtain a weighted autofluorescence image and subtracting, from each pixel value of the channel, the corresponding pixel value of the weighted autofluorescence image to obtain the corrected channel image. FIG. 26 shows an example of an MPX image of a pancreatic tissue sample before (top left) and after (bottom right) such correction.

Figure 11:
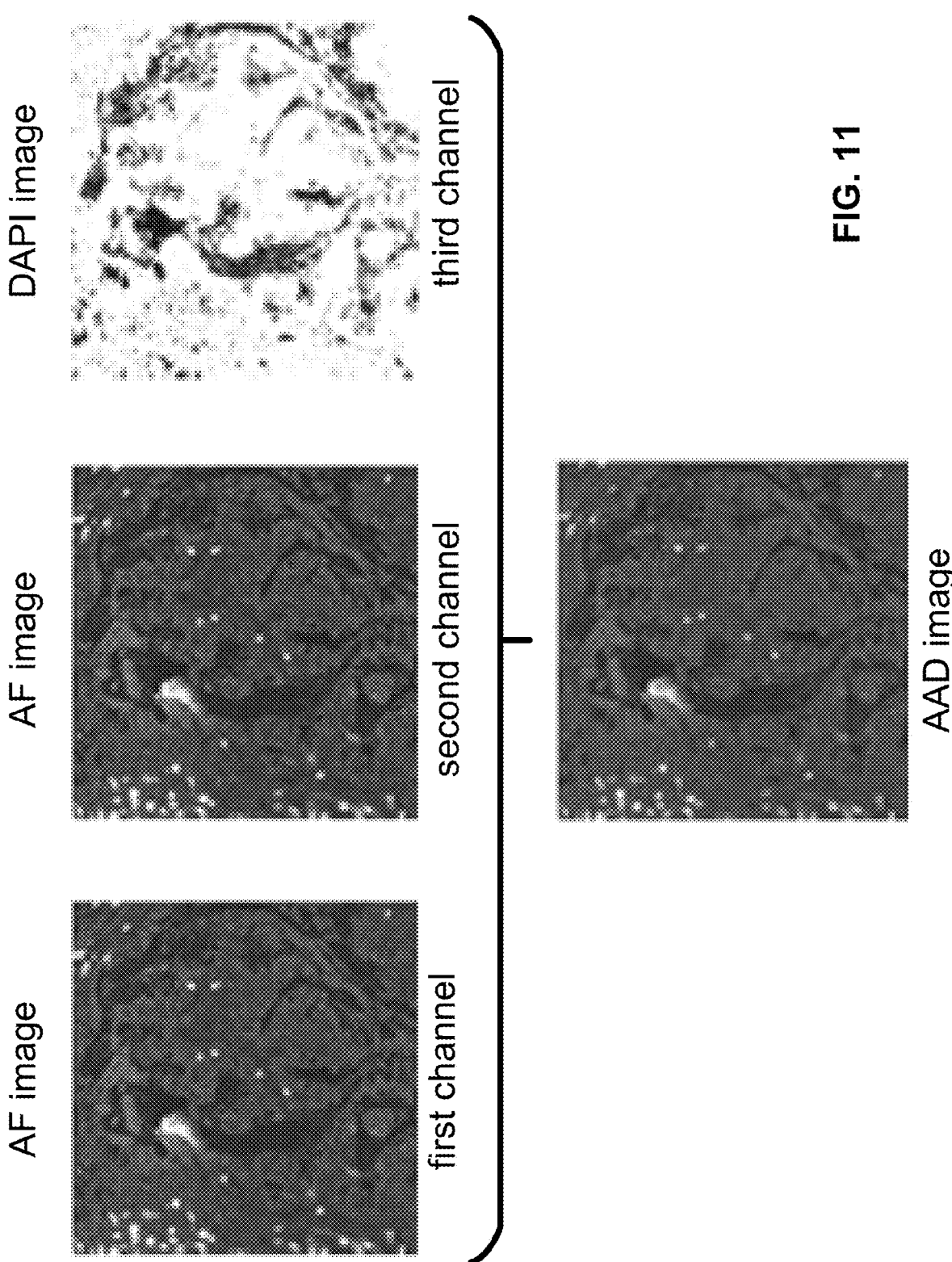
FIG. 11 illustrates a process of producing a three-channel mapped input image (e.g., for training deep-learning networks and/or for inference) according to some embodiments.
Figure 12:
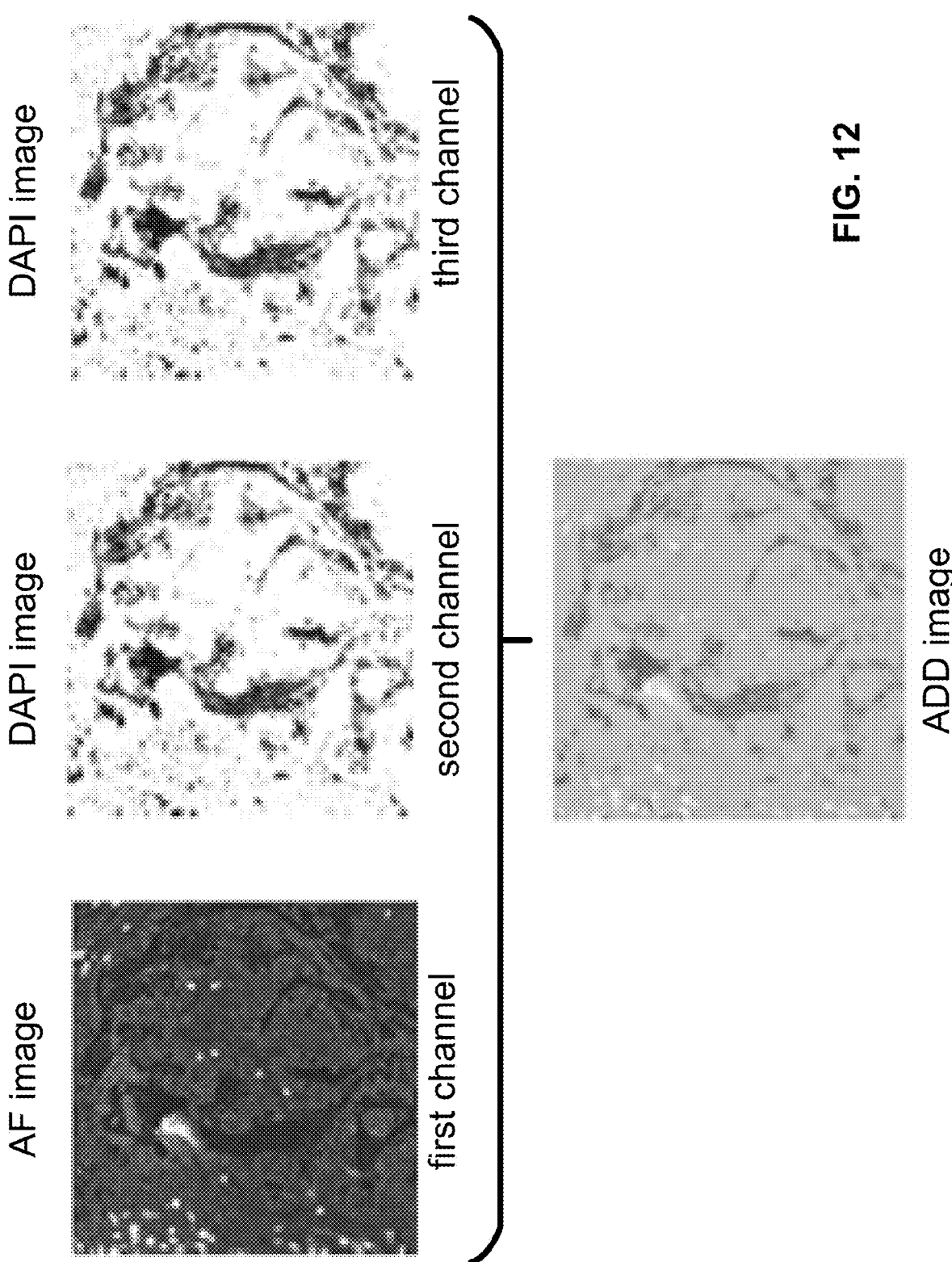
FIG. 12 illustrates another process of producing a three-channel mapped input image according to some embodiments.

As shown in FIGS. 11 and 12, the mapped input image may be produced as a linear combination of the autofluorescence image and the DAPI image. FIG. 11 illustrates an example of a process of producing a three-channel mapped input image according to some embodiments. In this example (corresponding to the mapped input image 'AAD' or 'AF+AF+DAPI' as shown in FIG. 10A), the first channel of the input image is the autofluorescence image, the second channel of the input image is also the autofluorescence image, and the third channel of the input image is the DAPI image. The three channels of an AAD image may be paired to the color channels (e.g., RGB) of real H&E images as training data for the GAN framework. The three channels of RGB will map to the three channels of AAD images.

FIG. 12 illustrates another example of a process of producing a three-channel mapped input image according to some embodiments. In this example (corresponding to the mapped input image 'ADD' or 'AF+DAPI+DAPI' as shown in FIG. 10B), the first channel of the input image is the autofluorescence image, the second channel of the input image is the DAPI image, and the third channel of the input image is also the DAPI image. Each of the three channels of an ADD image may be paired with a corresponding color channel of a real H&E image as training data for the GAN framework. For example, the three channels of an ADD image may be mapped to R, G, and B channels, respectively, of an actual H&E image.

Alternatively, the mapped input image may be produced from an optical density array that is a linear combination of the autofluorescence image and the DAPI image. Such a calculation may be based, for example, on the Lambert-Beer law, which describes the attenuation of light by a material through which the light is traveling. For a given wavelength c and a given stain s, this relation may be expressed as: [transmitted light intensity at wavelength c]=[incident light intensity at wavelength c]*exp(−[optical density of stained tissue at wavelength c]), where ODc=(amount of stain s in the tissue)*(absorption factor of stain s at wavelength c).

Such an embodiment of process block 804 may include generating an array of optical density values (e.g., an N-channel array of optical density values) as a linear combination of the autofluorescence image and the DAPI image, and applying a nonlinear function to the array of optical density values (also called an "optical density array") to obtain the mapped input image. Generating the optical density array as a linear combination of the autofluorescence image and the DAPI image may be performed, for example, as follows:

$$OD\_R = dapiwt[1]*DAPI + afwt[1]*AF;$$

$$OD\_G = dapiwt[2]*DAPI + afwt[2]*AF;$$

$$OD\_B=dapiwt[3]*DAPI+afwt[3]*AF;$$

where OD_R, OD_G, and OD_B denotes red, green, and blue channels of the optical density array; DAPI denotes the DAPI image; AF denotes the autofluorescence image; and dapiwt and afwt denote three-element weighting vectors. In some cases, it may be desired to adjust one or more channels of the optical density array (e.g., to subtract the bleed-through density within a neighbor spectrum).

The values of dapiwt and afwt may be selected experimentally (e.g., by visual inspection of the resulting mapped images and comparison of these images to actual H&E images). In one such example, the optical density array for the input image pHE as shown in FIG. 10C is obtained using the weighting vectors dapiwt=[29.2500 48.7500 14.6250] and afwt=[0.3900 23.5535 16.6717].

Alternatively, the values of dapiwt and afwt may be selected according to the color-dependent absorption characteristics of hematoxylin and eosin. In one such example, the optical density array for the input image pHE2 as shown in FIG. 10D is obtained using the weighting vectors dapiwt=w_D*Abs_Hem and afwt=w_A*Abs_Eos, where Abs_Hem is a color vector whose elements indicate the relative absorbances of hematoxylin for red, green, and blue light (e.g., [0.65 0.70 0.29]), Abs_Eos is a color vector whose elements indicate the relative absorbances of eosin for red, green, and blue light (e.g., [0.07 0.99 0.11]), and the sum of the scalar weights w_D and w_A is one (with default values w_D=w_A=0.5). FIG. 13 illustrates an example of such a process of producing a three-channel mapped input image according to some embodiments. In some cases, it may be desired to increase the value of w_D relative to w_A (e.g., to increase the influence of cell nuclei in the mapped input image).

Obtaining the mapped input image from the array of optical density values may include applying a nonlinear function (e.g., an exponential function) to convert the array of optical density values to an array of transmission values (also called a "transmission array"). Such a conversion may be performed, for example, as follows:

$$T\_R=exp(-OD\_R);$$

$$T\_G=exp(-OD\_G);$$

$$T\_B=exp(-OD\_B);$$

where T_R, T_G, and T_B denotes red, green, and blue channels of the array of transmission values. In another example of the nonlinear function, the base of the exponential function is ten rather than the Napierian constant e.

The values of the transmission array may be rescaled to the desired image space to obtain the mapped input image as a bright-field image. In one example, each value of the transmission array is scaled (e.g., multiplied) by a factor of 255 to obtain the mapped input image as a 24-bit RGB image. In another example, the values of the transmission array are normalized to the desired range (e.g., the range of from 0 to 255) by min-max scaling. Other output image spaces for the mapped input image may include an Lab color space (e.g., CIELAB, Hunter Lab, etc.) or a YCbCr color space (e.g., YCbCr. Y'CbCr, etc.), and producing the mapped input image from the transmission array may include converting from one color space to another (e.g., from RGB or sRGB to YCrCb or Y'CrCb).

Figure 14:
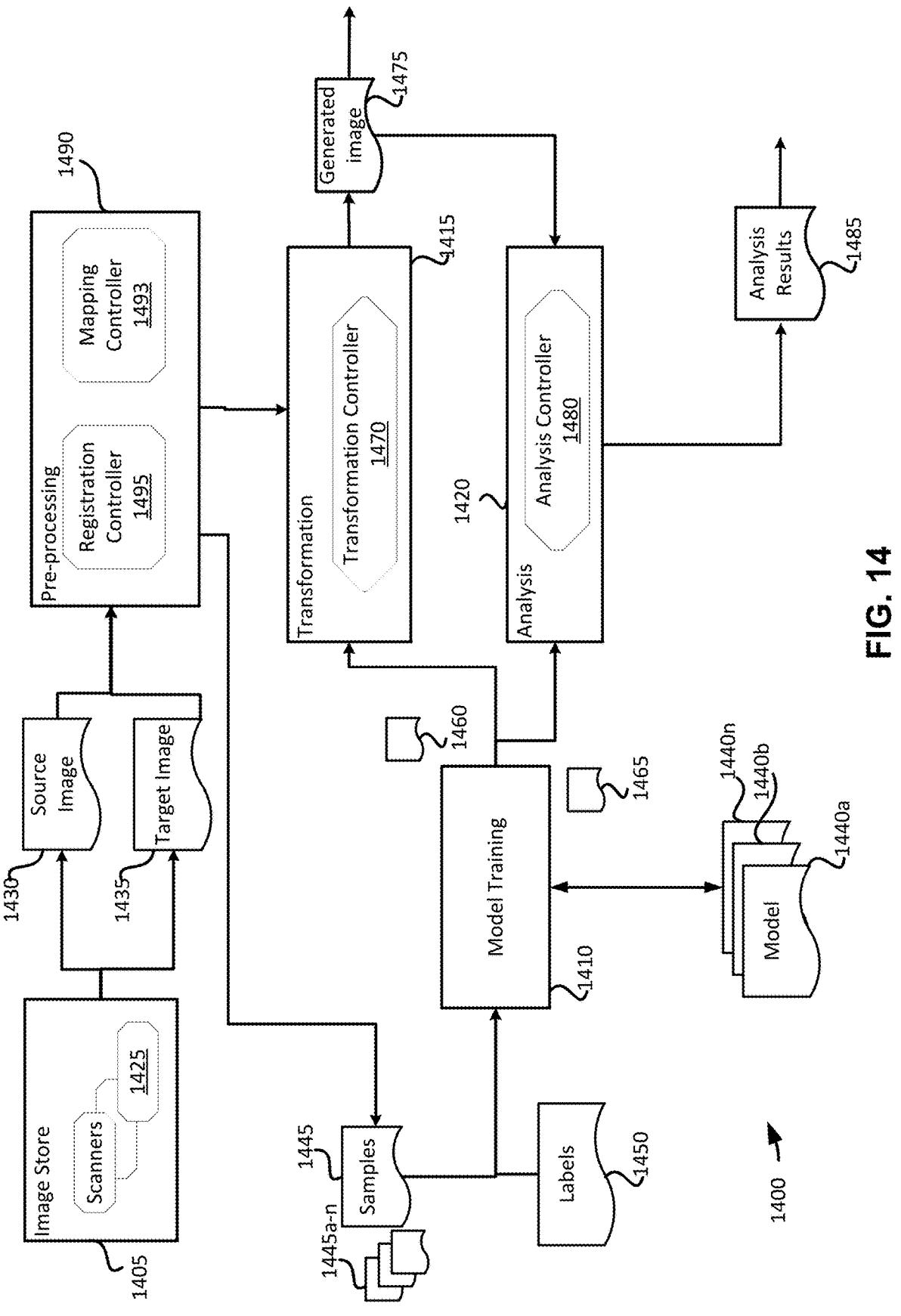
FIG. 14 illustrates an example computing environment according to some embodiments.

FIG. 14 illustrates an example computing environment 1400 (i.e., a data processing system) for transforming an MPX image of a tissue section into a synthetic image that depicts a tissue section that has been stained with at least one histochemical stain according to various embodiments. As shown in FIG. 14, the transforming performed by the computing environment 1400 in this example includes several stages: an image store stage 1405, a pre-processing stage 1490, a model training stage 1410, a transformation stage 1415, and an analysis stage 1420. The image store stage 1410 may include one or more digital image scanners or databases 1425 that are accessed (e.g., by pre-processing stage 1490) to provide a source set of digital images 1430 and a target set of digital images 1435 from preselected areas or the entirety of the biological sample slides (e.g., tissue slides).

The model training stage 1410 builds and trains one or more models 1440a-1440n ('n' represents any natural number) (which may be referred to herein individually as a model 1440 or collectively as the models 1440) to be used by the other stages. The model 1440 can be a machine-learning ("ML") model, which may include a convolutional neural network ("CNN"), an inception neural network, a residual neural network ("Resnet"), a U-Net, a V-Net, a single shot multibox detector ("SSD") network, a recurrent neural network ("RNN"), a deep neural network, a rectified linear unit ("ReLU"), a long short-term memory ("LSTM") model, a gated recurrent units ("GRUs") model, the like, or any combination thereof. In various embodiments, a generative model is configured with parameters that were learned by training a model 1440 that is capable of learning any kind of data distribution using unsupervised learning, such as a Generative Adversarial Network ("GAN"), a deep convolutional generative adversarial network ("DCGAN"), variation autoencoders (VAEs), a hidden Markov model ("HMM"), Gaussian mixture model, Boltzmann machine, the like, or combinations of one or more of such techniques—e.g., VAE-GAN. The computing environment 1400 may employ the same type of model or different types of models for transforming source images into generated images. In certain instances, the generative model is configured with parameters that were learned by training a model 1440 that is a GAN constructed with a loss function that tries to classify if the output image is real or fake, while simultaneously training a generative model to minimize this loss.

Figure 15:
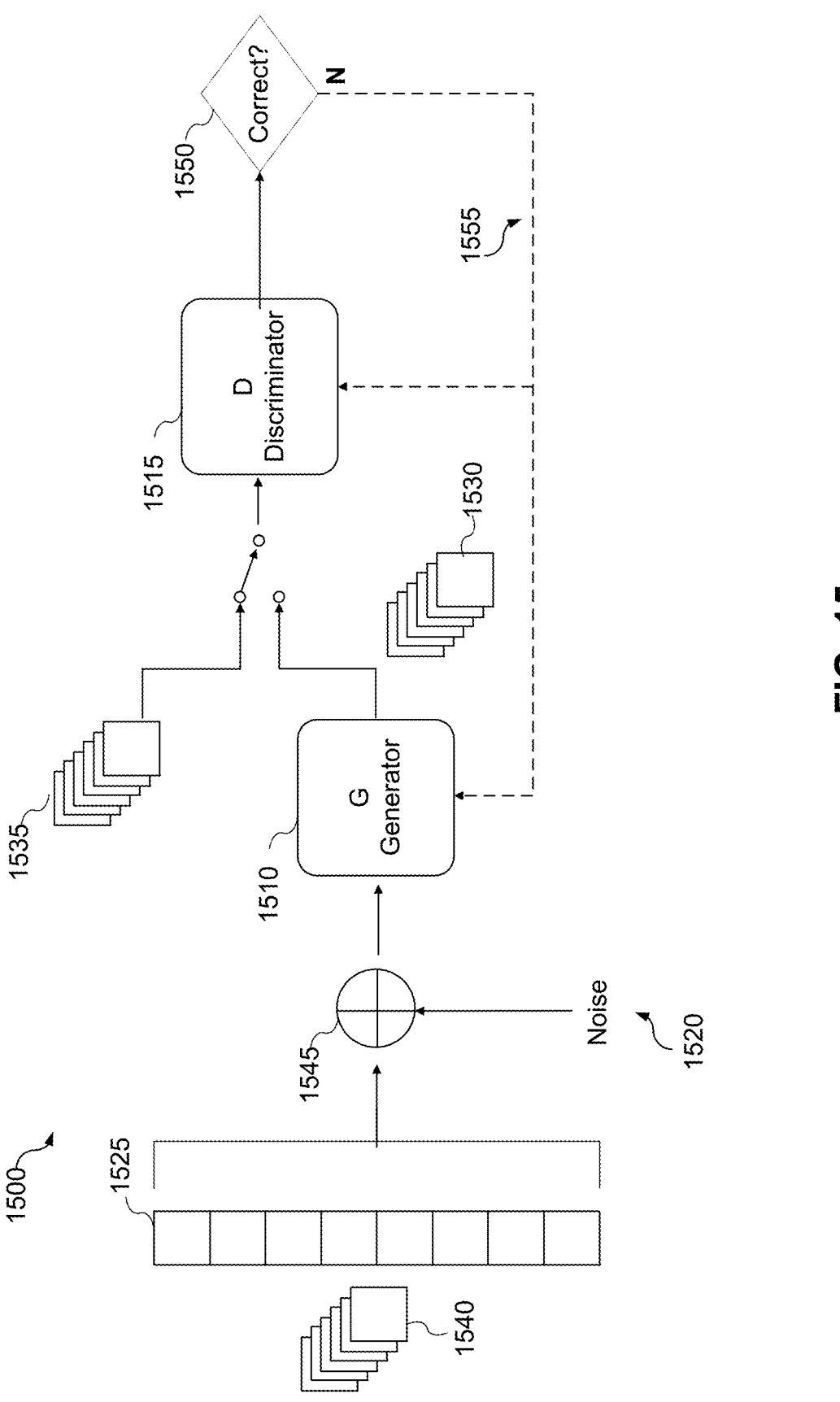
FIG. 15 illustrates a conditional GAN model according to some embodiments.

In an exemplary embodiment shown in FIG. 15, the model 1440 that is trained to provide the learned parameters is part of a conditional GAN ("cGAN") 1500, which is an extension of the GAN model, and generates images that have certain conditions or attributes. A cGAN learns a structured loss that penalizes the joint configuration of the output. Referring to FIG. 15, the cGAN 1500 includes a generator 1510 and a discriminator 1515. The generator 1510 is a neural network (e.g., a CNN) that takes a randomly generated noise vector 1520 and a latent feature vector (or a one-dimensional vector) 1525 (the condition, e.g., in the present instance, the mapped input image) as input data and feedback from the discriminator 1515 and generates new images 1530 that are as close to real target images 1535 as possible. The discriminator 1515 is a neural network (e.g., a CNN) configured as a classifier to determine whether the generated image 1530 from the generator 1510 is a real image or a fake image. The latent feature vector 1525 or the condition is derived from an input image or set of input images 1540 (e.g., images provided by mapping controller 1593), which encode the class (e.g., N-channel images obtained from M channels of corresponding MPX images according to a selected mapping) or a set of specific characteristics expected from the input image 1540. The randomly generated noise vector 1520 may be generated from a Gaussian distribution, and the vector space may be comprised of latent variables or hidden variables that are important for the domain but not directly observable. The latent feature vector 1525 and the random noise vector 1520 may be combined as input 1545 to the generator 1510. Alternatively or additionally, the noise may be added within the generator 1510 in the form of dropouts (e.g., probabilistically dropping inputs to a layer).

The generator 1510 receives the combined input 1545 and generates the image 1530 based on the latent feature vector 1525 and the random noise vector 1520 in the problem domain (i.e., domain of characteristics associated with target images 1535 that have been histochemically stained). The discriminator 1515 performs conditional-image classification by taking both a target image 1535 and a generated image 1530 as input and predicts 1550 the likelihood of whether the generated image 1530 is real or a fake translation of the target image 1535. The output of discriminator 1515 depends on the size of the generated image 1530 but may be one value or a square activation map of values. Each value is a probability for the likelihood that a patch in the generated image 1530 is real. These values can be averaged to give an overall likelihood or classification score if needed. The loss function of both the generator 1510 and discriminator 1515 may be configured such that the loss is dependent on how well the discriminator 1515 performs its job of predicting 1550 the likelihood of whether generated image 1530 is real or a fake translation of the target image 1535. After sufficient training, the generator 1510 will begin to produce generated images 1530 that look more like the target images 1535. Training of the GAN 1500 may proceed for a predefined number of training instances, and the resulting learned parameters may be accepted so long as one or more performance metrics (e.g., accuracy, precision, and/or recall) determined using a training or validation set exceed corresponding thresholds. Alternatively, training of the GAN 1500 may proceed until one or more performance metrics associated with recent training iterations exceed corresponding thresholds. At this point, the generated images 1530 may be sufficiently similar to the target images 1535 that the discriminator is no longer able to discern real from fake. Once the generator network 1510 has been trained, an input set of N-channel images (obtained from M channels of corresponding MPX images according to the selected mapping) may be input into the GAN 1500 to transform the input set of images into a new generated set of images with their characteristics similar to a target set of images obtained from slides that have been histochemically stained (e.g., H&E-stained). Thereafter, the new generated set of images can be used by a pathologist to visualize tissue structure during annotation of an MPX image (e.g., by toggling the MPX image or the synthetic H&E image on and off), to confirm a diagnosis that is based on an MPX image, and/or to register one MPX image to another MPX image (e.g., to support analysis based on a composite panel of biomarkers), etc.

With reference back to FIG. 14, to train model 1440 in this example, pre-processing stage 1490 generates samples 1445 by obtaining digital images (a source set of digital images 1430 and a target set of digital images 1435), mapping the source images to N-channel images according to a selected mapping (e.g., by mapping controller 1493), splitting the images into pairwise subsets of images 1445a (at least one pair of a mapped image and a target image) for training (e.g., 90%) and pairwise subsets of images 1445b for validation (e.g., 10%), preprocessing the pairwise subsets of images 1445a and the pairwise subset of images 1445b, augmenting the pairwise subset of images 1445a, and possibly in some instances annotating the pairwise subset of images 1445a with labels 1450. The pairwise subset of images 1445a may be obtained, for example, from a data storage structure such as a database or image server. Each image depicts a biological sample such as tissue.

The splitting may be performed randomly or pseudo-randomly (e.g., using a 90%/10%, 80%/20%, or 70%/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. The preprocessing may comprise cropping the images such that each image only contains a single object of interest. In some instances, the preprocessing may further comprise standardization or rescaling (e.g., normalization) to put all features on a same scale (e.g., a same size scale or a same color scale or color saturation scale). In certain instances, the images are resized with a minimum size (width or height) of predetermined pixels (e.g., 2500 pixels) or with a maximum size (width or height) of predetermined pixels (e.g., 3000 pixels) and kept with the original aspect ratio.

For example, pre-processing stage 1490 may prepare multiple patched images from a source set and a target set as one or more pairwise subsets of images for training data. The preparation of the paired images may comprise accessing matched pairs of a source image and a target image, in which the source image and the target image of each matched pair are from slides of nearby (e.g., adjacent or nearly adjacent) sections of the same biological sample (e.g., a tumor sample), the section depicted in the source image has been stained with a plurality of (e.g., 2, 3, 4, 5, or 6 or more) selected IHC fluorophores, and the section depicted in the target image has been stained with one or more selected histochemical stains. In one non-limiting example, the sections in each of the source images have been stained with six fluorophores (including a nuclear counterstain, e.g., DAPI), and the sections in each of the target images have been stained with H&E. FIGS. 5A and 5B show one example of a matched pair of a dark-field MPX image of an IHC-stained tissue section (FIG. 5A) and a bright-field image of a nearby (e.g., adjacent) section of the same tissue sample that has been H&E-stained (FIG. 5B).

Pre-processing stage 1490 may then map each of the source images (e.g., by mapping controller 1493) according to a selected mapping to obtain an N-channel input image that is paired with a corresponding target image, and divide each of the paired input and target images (e.g., whole slide images) into a number of patches of a predetermined size (e.g., 128×128, 256×256, or another size) to produce matched pairs of patches for training. It may be desired to use only patches that are from regions of interest within the images, such as tumor annotations that have been added, for example, by a reviewing pathologist. Pre-processing stage 1490 (e.g., registration controller 1495) may perform alignment and/or registration of the paired input and target images before and/or after the images are divided into patches. Alignment may comprise designating one image as the reference image, also called the fixed image, and applying geometric transformations or local displacements to the other image so that the other image aligns with the reference image. Because the histochemically stained images (i.e., the target images) provide the ground truth for training the network, it may be desired to designate the target images as the reference images for purposes of alignment and registration. Aligned pairs of patches from the input set and the target set are selected, and this process results in one or more pairwise subsets of images for training data. Pre-processing stage 1490 may input the patch pairs to the GAN or cGAN to train the deep learning network.

With respect back to FIG. 14, pre-processing stage 1490 may use augmentation to artificially expand the size of the pairwise subset of images 1445*a* by creating modified versions of images in the datasets. Image data augmentation may be performed by creating transformed versions of images in the datasets that belong to the same class as the original image. Transforms include a range of operations from the field of image manipulation, such as shifts, flips, zooms, and the like. In some instances, the operations include random erasing, shifting, brightness, rotation, Gaussian blurring, and/or elastic transformation to ensure that the model 1440 is able to perform under circumstances outside those available from the pairwise subset of images 1445*a*.

The training process for model 1440 includes performing iterative operations of inputting images from the pairwise subset of images 1445*a* into the model 1440 to find a set of model parameters (e.g., weights and/or biases) that minimizes one or more loss or error functions for the model 1440 (e.g., a first loss function to train the discriminator to maximize the probability of the image training data and a second loss function to train the discriminator to minimize the probability of the generated image sampled from the generator and train the generator to maximize the probability that the discriminator assigns to its own generated image). Prior to training, the model 1440 is configured with a defined set of hyperparameters, which are settings that are external to the model and can be tuned or optimized to control the behavior of the model 1440. For most models, hyperparameters are explicitly defined to control different aspects of the models, such as memory or cost of execution, for example. However, additional hyperparameters may be defined to adapt a model to a specific scenario. For example, the hyperparameters may include the number of hidden units of a model, the learning rate of a model, the convolution kernel width, or the number of kernels for a model. Each iteration of training can involve finding a set of model parameters for the model 1440 (as configured with a corresponding defined set of hyperparameters) so that the value of the loss or error function using the set of model parameters is smaller than the value of the loss or error function using a different set of model parameters in a previous iteration. As opposed to hyperparameters, the model parameters are variables that are internal to the model, and their values may be estimated (e.g., learned) from the training data. The loss or error function can be constructed to measure the difference between the outputs inferred using the models 1440 and the ground truth target images using the labels 1450.

Once the set of model parameters is identified, the model 1440 has been trained and can be validated using the pairwise subset of images 1445*b* (testing or validation data set). The validation process includes iterative operations of inputting images from the pairwise subset of images 1445*b* into the model 1440 using a validation technique such as K-Fold Cross-Validation, Leave-one-out Cross-Validation, Leave-one-group-out Cross-Validation, Nested Cross-Validation, or the like to tune the hyperparameters and ultimately find an optimal set of hyperparameters. Once the optimal set of hyperparameters is obtained, a reserved test set of images from the subset of images 1445*b* are input into the model 1440 to obtain output (in this example, generated images with characteristics similar to a target image), and the output is evaluated versus ground truth target images using correlation techniques such as Bland-Altman method and the Spearman's rank correlation coefficients and calculating performance metrics such as the error, accuracy, precision, recall, receiver operating characteristic curve (ROC), etc.

As should be understood, other training/validation mechanisms are contemplated and may be implemented within the computing environment 1400. For example, the model 1440 may be trained and hyperparameters may be tuned on images from the pairwise subset of images 1445*a* and the images from the pairwise subset of images 1445*b* may be used only for testing and evaluating performance of the model 1440.

The model training stage 1410 outputs trained models including one or more trained transformation models 1460 and optionally one or more image analysis models 1465. In some instances, a first model 1460*a* has been trained to process an input image obtained from a source image 1430 of a biological specimen (a tissue section). The input image is an N-channel image obtained from M channels of an MPX image of the biological specimen according to a selected mapping. The input image is obtained by a transformation controller 1470 within the transformation stage 1415. The transformation controller 1470 includes program instructions for transforming, using the one or more trained transformation models 1460, the input image into a new image 1475 having the characteristics of a target image. The characteristics of the target image are associated with an image of a tissue section that has been stained with one or more selected histochemical stains (e.g., H&E). The transformation includes inputting the input image into a trained generator model (part of transformation model 1460) and generating, by the generator model, a new image 1475.

In some instances, the new image 1475 is transmitted to an analysis controller 1480 within the analysis stage 1420. The analysis controller 1480 includes program instructions for analyzing, using the one or more image analysis models 1465, the biological sample within the new image 1475; and outputting an analysis result 1485 based on the analyzing. The analyzing of the biological sample within the new image 1475 may comprise extracting measurements based on area within the new image 1475, one or more cells within the new image 1475, and/or objects in the new image 1475 aside from cells. Area-based measurements may include the most basic assessments, for example, quantifying the area (2-dimensional) of a certain stain (e.g., histochemical stain), the area of fat vacuoles, or other events present on a slide. Cell-based measurements aim at identifying and enumerating objects, e.g. cells. This identification of individual cells enables subsequent assessment of subcellular compartments. Finally, algorithms can be utilized to assess events or objects present on tissue sections that may not be comprised of individual cells. In certain instances, the imaging analysis algorithms are configured to locate cells or subcellular structures, and provide a quantitative representation of cell staining, morphology, and/or architecture that can ultimately be used to support diagnosis and prediction. In some instances, the imaging analysis algorithms are configured specifically for analysis of images having characteristics of the target images (e.g., images of sections that have been histochemically stained). For example, the analysis of the new image 1475 may include providing, for the corresponding MPX source image, an automated delineation of ROIs and/or regions to be excluded. In another example, the analysis of the new image 1475 may include registering the new image 1475 with another new image 1475 and applying the registration results to the corresponding MPX source images.

While not explicitly shown, it will be appreciated that the computing environment 1400 may further include a developer device associated with a developer. Communications from a developer device to components of the computing environment 1400 may indicate what types of input images are to be used for the models, a number and type of models to be used, hyperparameters of each model, for example, learning rate and number of hidden layers, how data requests are to be formatted, which training data is to be used (e.g., and how to gain access to the training data) and which validation technique is to be used, and/or how the controller processes are to be configured.

Figure 16:
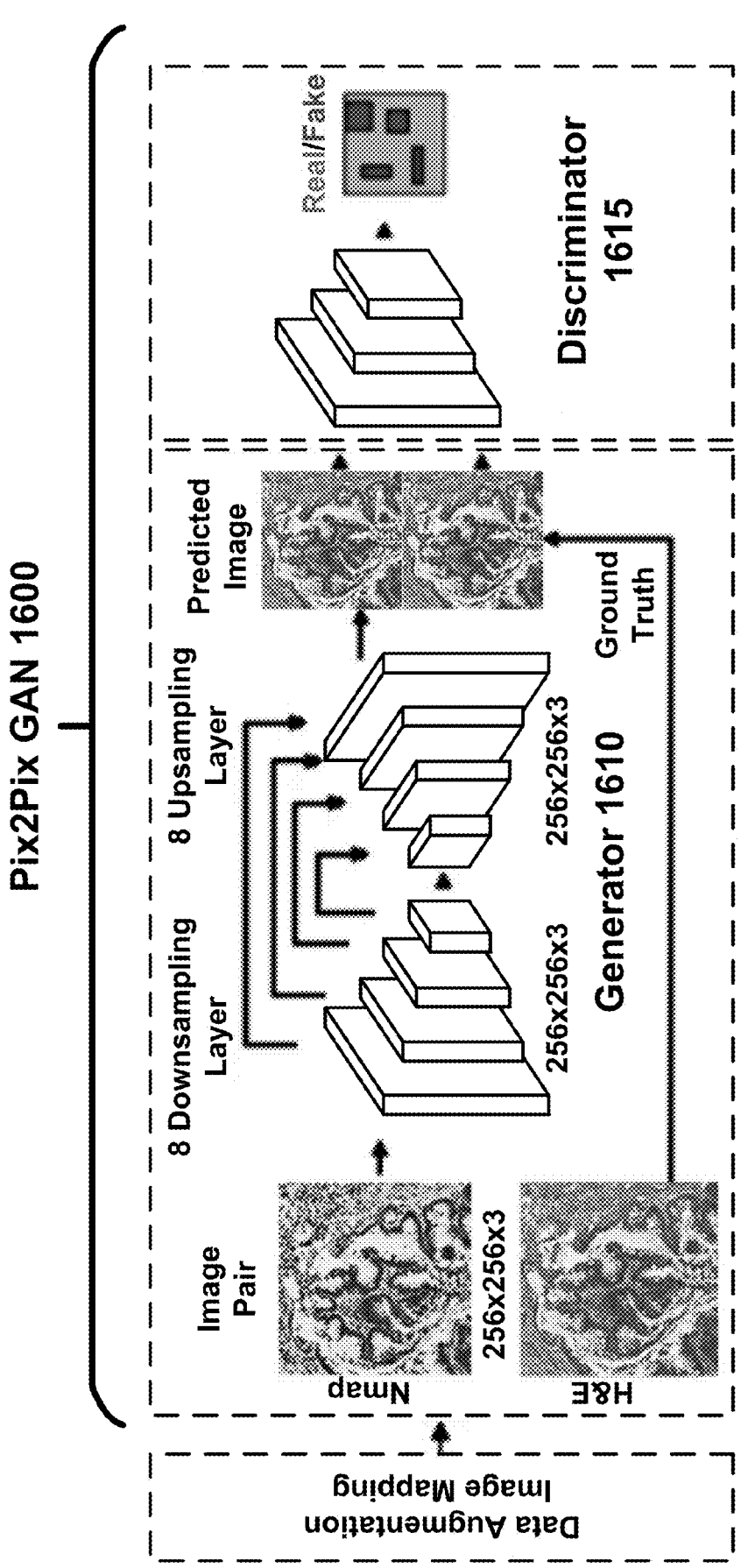
FIG. 16 shows an example of an implementation of a conditional GAN model that uses a Pix2Pix GAN according to some embodiments.

One particular example of a cGAN model 1500 that may be used to train the generator network 1510 is a Pix2Pix GAN. FIG. 16 shows an example of an implementation of cGAN model 1500 that uses a Pix2Pix GAN 1600 to train a generator network 1610 to translate N-channel images, each obtained from M channels of a corresponding MPX image of an IHC-stained tissue section according to a selected mapping, into synthetic images of histochemically stained (e.g., H&E-stained) tissue sections. As illustrated in FIG. 16, the generator network 1610 is implemented using a U-Net architecture, which includes an encoder having layers that progressively downsample the input to a bottleneck layer, and a decoder having layers that progressively upsample the bottleneck output to produce the output. As shown in FIG. 16, the U-Net also includes skip connections between encoder and decoder layers having equally sized feature maps; these connections concatenate the channels of the feature map of the encoder layer with those of the feature map of the corresponding decoder layer. In a particular example, the generator network 1610 is updated via L1 loss measured between the generated image and the expected output image (e.g., the "predicted image" and the "ground truth," respectively, in FIG. 16).

Figure 17:
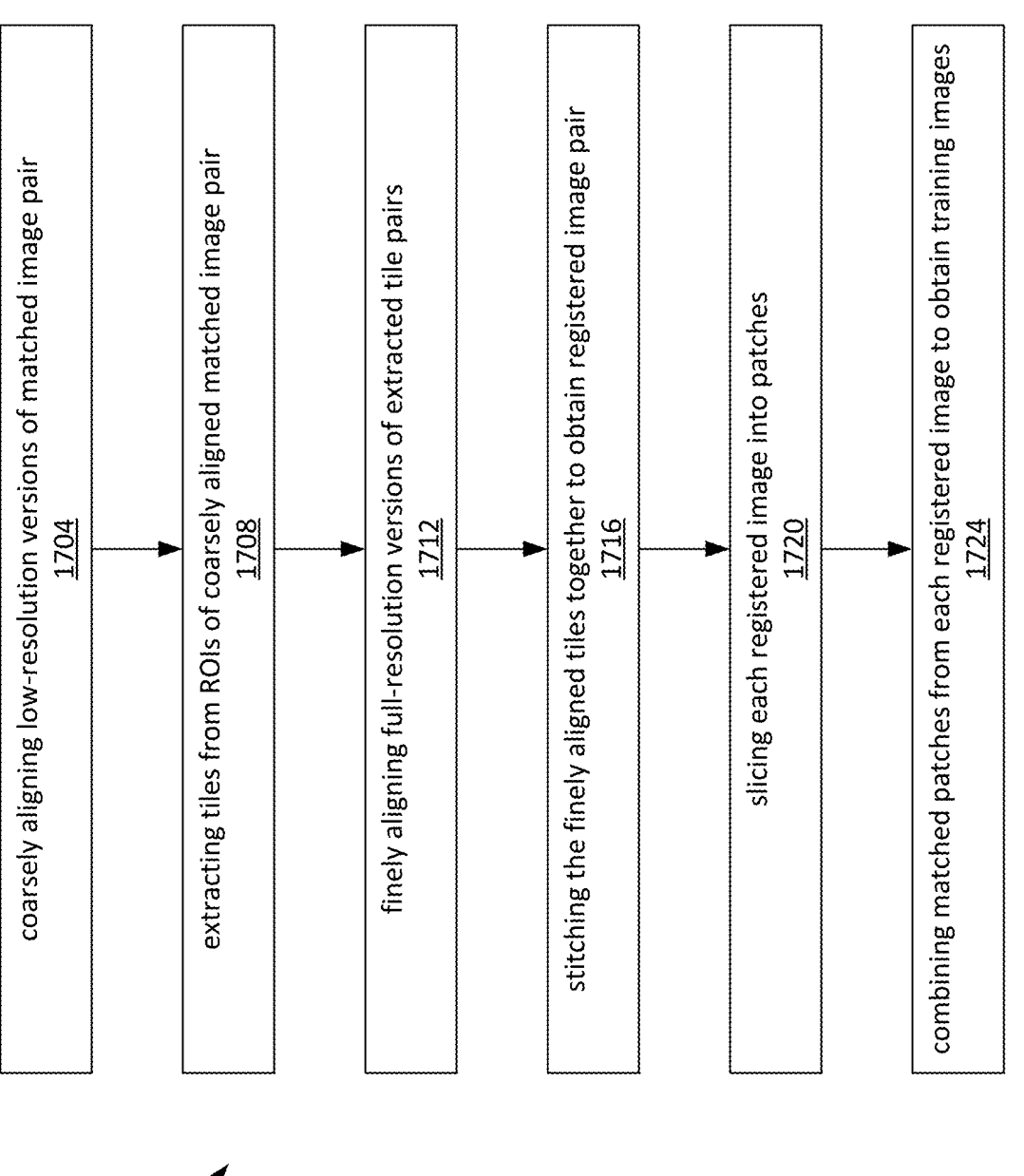
FIG. 17 illustrates a flowchart for a process of obtaining training images according to some embodiments.

Generally, use of a Pix2Pix GAN requires that the matched pairs of image patches that are to be used to train the generator network have been registered (e.g., at the pixel level). FIG. 17 illustrates a flowchart for an exemplary process 1700 to produce matched and registered pairs of image patches from a matched image pair as described herein (e.g., for training and/or validation). Process 1700 may be performed by pre-processing stage 1490 (e.g., by registration controller 1495). Referring to FIG. 17, at block 1704, low-resolution versions of the matched image pair are coarsely aligned. In one example, such coarse alignment may be performed by applying a transformation matrix Mc (e.g., including a translation and/or a rotation) to a low-resolution version of a N-channel mapping $I_{Nmap}$ of M channels of an MPX image of an IHC-stained section to align it to an image $I_{H\&E}$ of a matching (e.g., nearby) section that is H&E-stained. Transformation matrix Mc may be calculated automatically based on, for example, an outline of the tissue in each of the images to be aligned.

At block 1708, tiles are extracted from regions of interest (ROIs) of the coarsely aligned image pair (e.g., by projecting a grid onto each image that covers the annotations, and extracting corresponding tiles from each image). FIG. 18 shows an example of a tile $T_{Nmap}$ (e.g., of size 2048×2048 pixels) from an ROI of image $I_{Nmap}$ and a corresponding tile $T_{H\&E}$ (e.g., of size 2048×2048 pixels) from image $I_{H\&E}$. At block 1712, full-resolution versions of extracted tile pairs are finely aligned. Such fine alignment may include, for example, scaling, deskewing, and/or warping of a tile from one of the images (e.g., $I_{Nmap}$) to register it to the corresponding tile from the other image (e.g., $I_{H\&E}$ (the reference image as discussed above)). At block 1716, the finely aligned tiles are stitched together to obtain a registered image pair; at block 1720, each of the registered images is sliced into patches (e.g., of size 128×128 pixels, 256×256 pixels, or another size); and at block 1724, matched patches from each registered image (e.g., patches $P_{Nmap}$ and $P_{H\&E}$ as shown in FIG. 18) are combined (e.g., stitched together side-to-side) to obtain training images. For example, a pair of matching patches, each of size 128×128 pixels, may be stitched together to obtain a training image of size 128×256 pixels; or a pair of matching patches, each of size 256×256 pixels, may be stitched together to obtain a training image of size 256×512 pixels. In such manner, a process of stitching together finely-aligned tiles of each image to obtain a registered image pair, and combining matched patches from each of the registered images to obtain a set of training images, may be implemented to obtain sets of training data for using a Pix2Pix GAN implementation to train generator network 1510 to transform N-channel mapped images obtained from M channels of corresponding MPX images to synthetic images of histochemically stained sections.

Figure 19:
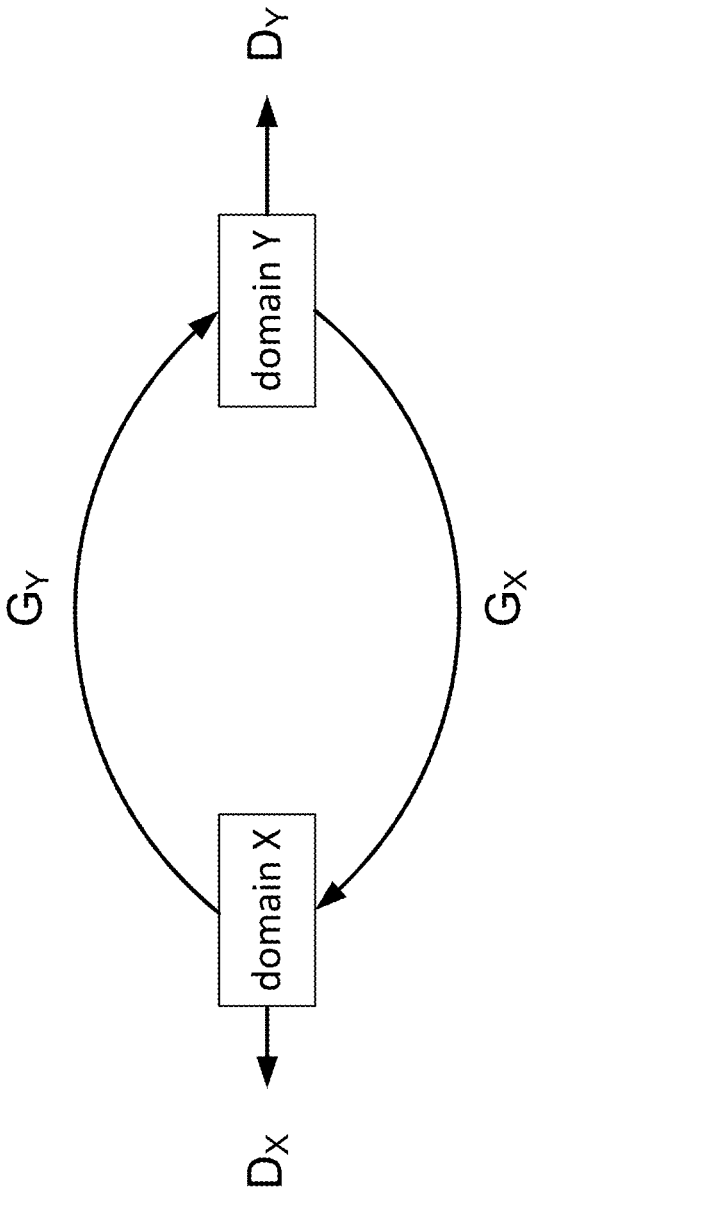
FIG. 19 shows a representation of networks and network connections in a Cycle-GAN according to some embodiments.

Another particular example of a cGAN model 1500 that may be used to train the generator network 1510 is a Cycle-GAN that includes multiple generator networks and multiple discriminator networks. FIG. 19 shows a representation of generator networks $G_X$ and $G_Y$ and discriminator networks $D_X$ and $D_Y$ in a Cycle-GAN. In this example, the Y domain corresponds to images depicting samples that have been histochemically stained, and the X domain corresponds to N-channel images obtained from M channels of corresponding MPX images of IHC-stained samples according to a selected mapping.

Figure 20:
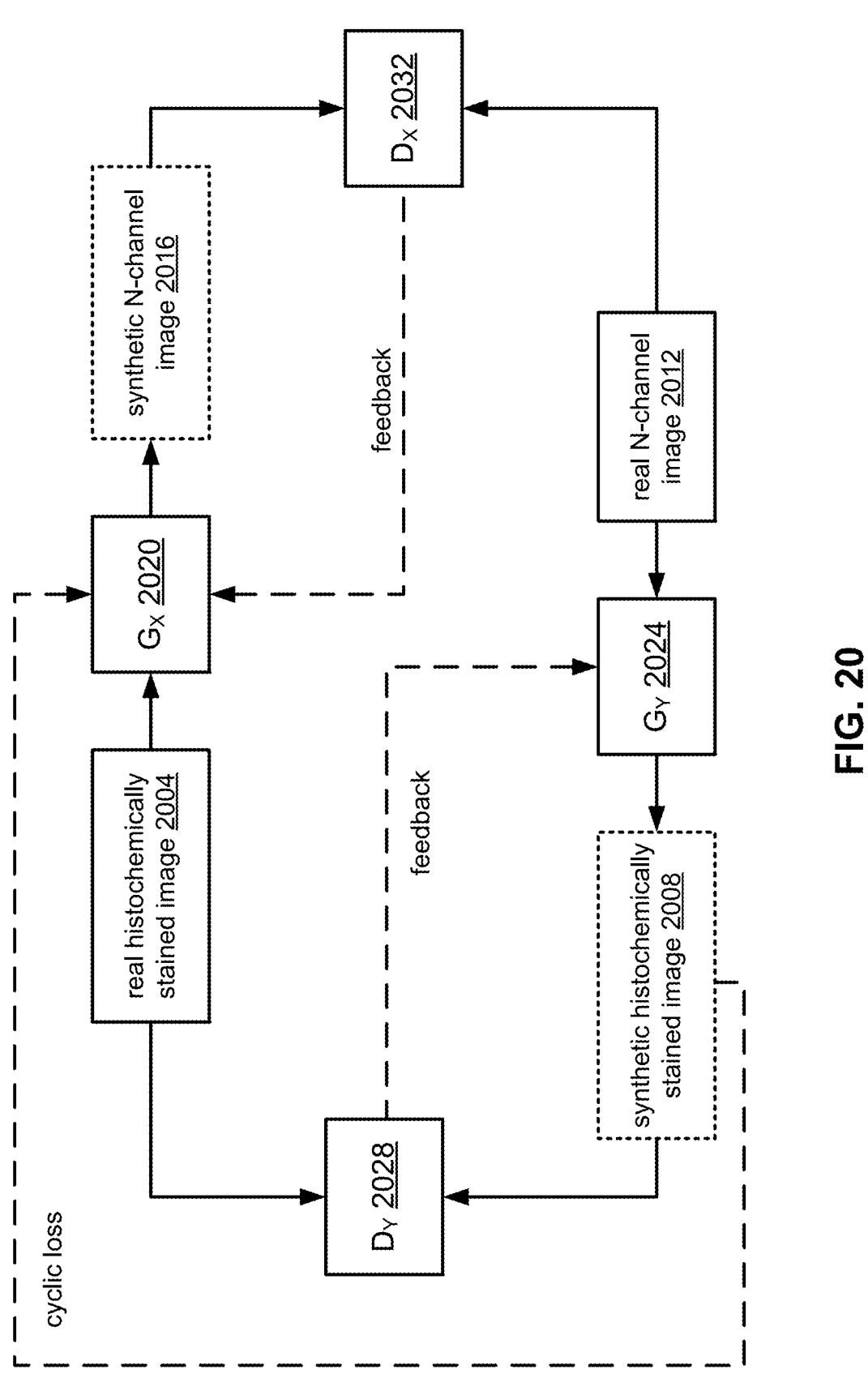
FIG. 20 illustrates a flow of generating and discriminating images using a Cycle-GAN according to some embodiments.

FIG. 20 illustrates a flow among the generator and discriminator networks in an application of a Cycle-GAN as described herein. The Cycle-GAN includes an X-to-Y generator network $G_Y$ 2024 (to be trained as generator network 1510) and also includes a Y-to-X generator network $G_X$ 2020 that is configured and trained to transform an image of a histochemically stained sample to an image depicting an N-channel mapping from M channels of an MPX image of an IHC-stained sample. The generator network $G_X$ 2020 can include one or more convolution layers and may include a U-net or a V-net. In some instances, the generator network $G_X$ 2020 includes a feature-extracting encoder, a transformer, and a decoder, each having one or more convolution layers. The architectures of the generator networks $G_X$ 2020 and $G_Y$ 2024 may be the same.

The Cycle-GAN includes a discriminator network $D_X$ 2032 that discriminates between real and fake images that depict an N-channel mapping from M channels of an MPX image of an IHC-stained sample (e.g., real N-channel image 2012 and fake N-channel image 2016) and another discriminator network $D_Y$ 2028 that discriminates between fake and real images that depict a histochemically stained sample (e.g., real histochemically stained image 2004 and fake histochemically stained image 2008). Each of the discriminator networks $D_X$ and $D_Y$ may include one or more convolution layers and an activation layer, and the architectures of the discriminator networks $D_X$ and $D_Y$ may be the same.

Use of a CycleGAN may have the advantage that fine registration of matched pairs of images (e.g., fine registration of images $I_{Nmap}$ and $I_{H\&E}$ as described herein with reference to FIGS. 17 and 18) is not required to generate the training data. However, better results were obtained when using a Pix2Pix GAN implementation to train generator network 1510 on image patches of paired registered images.

The methods according to the present disclosure may be implemented to transform images of MPX images into corresponding synthetic images of H&E-stained samples. Such methods may be used, for example, to assist a pathologist in the annotation of the MPX source image. Such a method may be implemented as a key part of a fast screening process to provide a reference image of underlying tissue structure without performing an actual H&E staining. Moreover, such "virtual staining" technology can also be used to confirm a diagnosis that is based on a corresponding MPX image. Even further, a method of image transformation as described herein may be used to support automated registration of MPX images to enable analysis (e.g., co-location, co-expression) of expanded panels of biomarkers.

Figure 21:
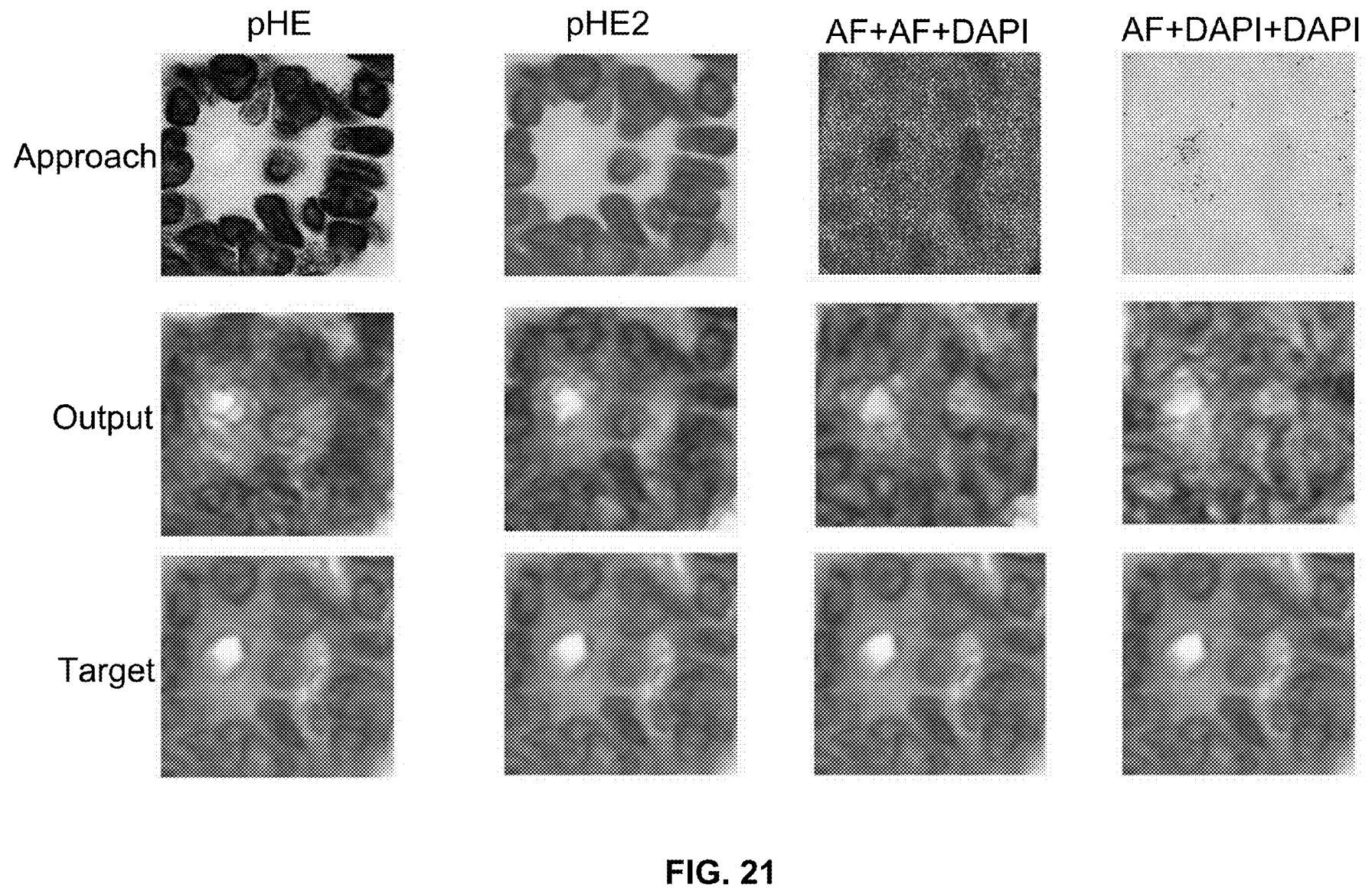
Figure 22:
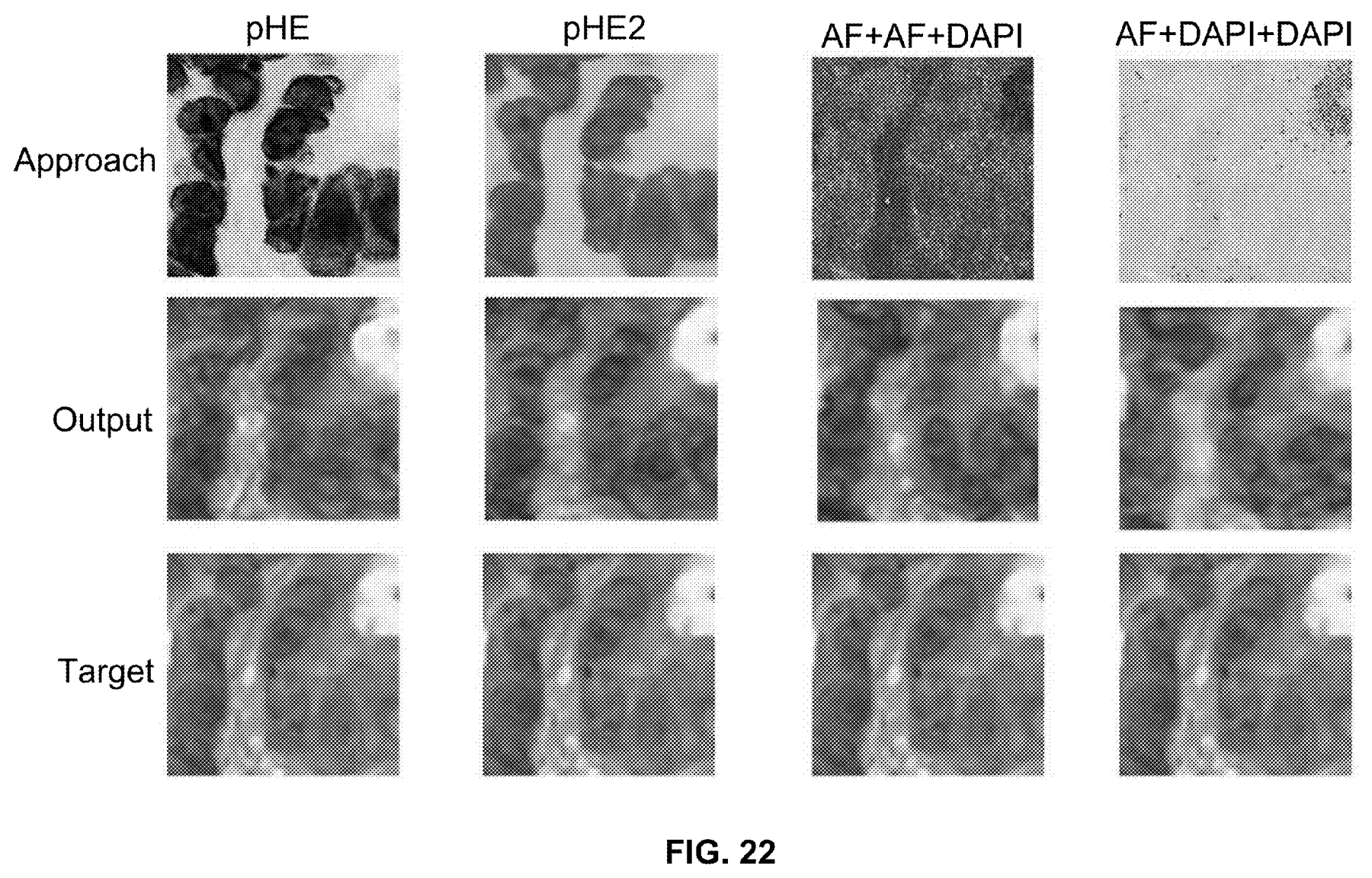
Figure 23:
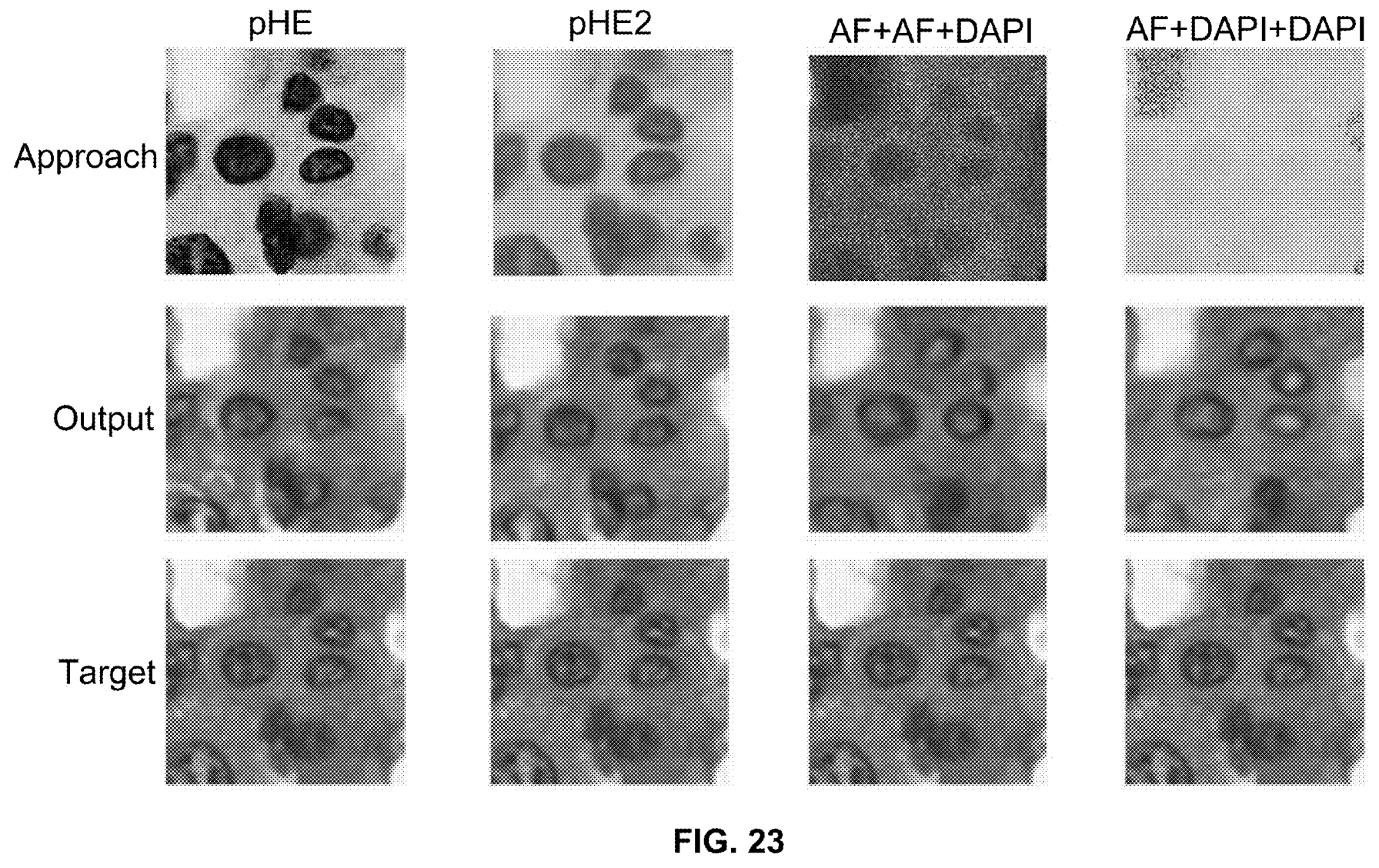

FIGS. 21-23 show three different examples, respectively, of using an implementation of process 800 (using a Pix2Pix GAN as described herein) to transform an MPX image into a corresponding synthetic H&E-stained image. Each of FIGS. 21-23 shows results obtained using each of the four example source image mappings (pHE, pHE2, AAD, ADD) as shown in FIGS. 10A-D and described herein. In each of FIGS. 21-23, the top row shows the N-channel mapped source image ('approach'), the middle row shows the corresponding generated synthetic H&E image ('output'), and the bottom row shows a corresponding actual H&E image ('target'). It may be seen that the output images are very similar to the target images.

V. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method of image transformation, the method comprising:
   producing an N-channel input image that is based on information from each of M channels of a multiplexed immunofluorescence (MPX) image of a tissue section, where M is a positive integer and N is a positive integer that is less than or equal to M; and
   generating a synthetic image by processing the N-channel input image using a generator network, the generator network having been trained using a training data set that includes a plurality of pairs of images,
   wherein the synthetic image depicts a tissue section that has been stained with at least one histochemical stain, and
   wherein, for each pair of images of the plurality of pairs of images, the pair includes:
      an N-channel image produced from an MPX image of a first section of a tissue, and
      an image of a second section of the tissue that has been stained with the at least one histochemical stain.

2. The method of claim 1, wherein producing the N-channel input image comprises, for each of the M channels of the MPX image of the tissue section, mapping information from the channel to at least one of the N channels of the N-channel image.

3. The method of claim 2, wherein the mapping includes producing an autofluorescence image that is based on information from each of a plurality of channels of the MPX image of the tissue section, and
   wherein the N-channel input image is based on information from the autofluorescence image.

4. The method of claim 3, wherein the autofluorescence image is based on a nonlinear combination of the plurality of channels of the MPX image of the tissue section.

5. The method of claim 3, wherein the autofluorescence image is based on a spectral distribution of autofluorescence among the plurality of channels.

6. The method of claim 3, wherein the plurality of channels of the MPX image is the M channels of the MPX image of the tissue section.

7. The method of claim 1, wherein, for each pair of images of the plurality of pairs of images, the N-channel image of the pair is based on information from each of M channels of the MPX image of the first section.

8. The method of claim 1, wherein the synthetic image is an N-channel image.

9. The method of claim 8, wherein each of the N-channel input image and the synthetic image is an RGB image.

10. The method of claim 1, wherein the MPX image of the tissue section is a dark-field image and the synthetic image is a bright-field image.

11. The method of claim 1, wherein the N-channel image is based on an autofluorescence image and on a channel of the MPX image of the tissue section that corresponds to a nuclear counterstain.

12. The method of claim 1, wherein the N-channel image is based on a linear combination of an autofluorescence image and a channel of the MPX image of the tissue section that corresponds to a nuclear counterstain.

13. The method of claim 12, wherein the N-channel image is based on an array of optical density values that is based on the linear combination.

14. The method of claim 1, wherein N is equal to three and M is at least four.

15. The method of claim 1, wherein the generator network was trained as part of a generative adversarial network.

16. The method of claim 1, wherein the generator network is implemented as a U-Net.

17. The method of claim 1, wherein the generator network is implemented as an encoder-decoder network.

18. The method of claim 1, further comprising:
predicting a diagnosis of a subject based on the synthetic image, wherein the tissue section was collected from the subject.

19. A system comprising:
one or more data processors; and
a non-transitory computer readable storage medium containing instructions which, when executed on the one or more data processors, cause the one or more data processors to perform a set of actions including:
producing an N-channel input image that is based on information from each of M channels of a multiplexed immunofluorescence (MPX) image of a tissue section, where M is a positive integer and N is a positive integer that is less than or equal to M; and
generating a synthetic image by processing the N-channel input image using a generator network, the generator network having been trained using a training data set that includes a plurality of pairs of images, wherein the synthetic image depicts a tissue section that has been stained with at least one histochemical stain, and
wherein, for each pair of images of the plurality of pairs of images, the pair includes:
an N-channel image produced from an MPX image of a first section of a tissue, and
an image of a second section of the tissue that has been stained with the at least one histochemical stain.

20. A computer-program product tangibly embodied in a non-transitory machine-readable storage medium, including instructions configured to cause one or more data processors to perform a set of actions including:
producing an N-channel input image that is based on information from each of M channels of a multiplexed immunofluorescence (MPX) image of a tissue section, where M is a positive integer and N is a positive integer that is less than or equal to M; and
generating a synthetic image by processing the N-channel input image using a generator network, the generator network having been trained using a training data set that includes a plurality of pairs of images,
wherein the synthetic image depicts a tissue section that has been stained with at least one histochemical stain, and
wherein, for each pair of images of the plurality of pairs of images, the pair includes:
an N-channel image produced from an MPX image of a first section of a tissue, and
an image of a second section of the tissue that has been stained with the at least one histochemical stain.

* * * * *